(12) United States Patent
Doherty et al.

(10) Patent No.: US 10,272,314 B2
(45) Date of Patent: Apr. 30, 2019

(54) COACHING AID FOR GOLF

(71) Applicant: SkyHawke Technologies, LLC, Ridgeland, MS (US)

(72) Inventors: Matthew P. Doherty, North Palm Beach, FL (US); James F. Doherty, III, Raleigh, NC (US); William G. Moore, Raleigh, NC (US)

(73) Assignee: SKYHAWKE TECHNOLOGIES, LLC, Ridgeland, MS (US)

( * ) Notice: Subject to any disclaimer, the term of this patent is extended or adjusted under 35 U.S.C. 154(b) by 0 days.

(21) Appl. No.: 15/870,359

(22) Filed: Jan. 12, 2018

(65) Prior Publication Data

US 2018/0133577 A1 May 17, 2018

Related U.S. Application Data

(63) Continuation of application No. 15/079,086, filed on Mar. 24, 2016, now Pat. No. 9,868,043, which is a
(Continued)

(51) Int. Cl.
 A63B 69/36 (2006.01)
 A63B 71/06 (2006.01)
(Continued)

(52) U.S. Cl.
 CPC .......... *A63B 69/36* (2013.01); *A63B 24/0021* (2013.01); *A63B 71/0622* (2013.01); *G09B 19/0038* (2013.01); *A63B 2024/0056* (2013.01); *A63B 2069/3605* (2013.01); *A63B 2071/0691* (2013.01); *A63B 2102/32* (2015.10); *A63B 2220/12* (2013.01); *A63B 2220/20* (2013.01);
(Continued)

(58) Field of Classification Search
 CPC ........ A63B 2243/0029; A63B 71/0622; A63B 69/36; H04N 21/4728
 See application file for complete search history.

(56) References Cited

U.S. PATENT DOCUMENTS 5,810,680 A 9/1998 Lobb et al.
5,816,953 A 10/1998 Cleveland
(Continued)

OTHER PUBLICATIONS

Bajek, Dan, "KNR 245," Apr. 29, 2013, downloaded from URL https://www.google.com/url?sa=t&rct=j&q=&esrc=s&source=web&cd=2*cad=rja&uact=8*ved=0CCYQFjABahUKEwi7xujKtj_HAhWMbT4KHWsIB2Y&url=http%3A%2F%2fwww.castonline.ilstu.edu%2Fhenninger%2FDocuments%2FKN$%2520245%2FGroup%2520ResourceSection%25203%2FGolf%FKNR_245_gold.doc&ei=HBHJVbvllozb-QHrkJyqBg&us.
(Continued)

*Primary Examiner* — Steven J Hylinski
(74) *Attorney, Agent, or Firm* — Neo IP

(57) ABSTRACT

Systems and methods providing statistical analytics of golf performance for coaching including text, tabular, graphic, and image-based outputs that include trends information for the golfer, all based upon actual golf play on course situations, wherein the golfer inputs shot data during play, without interrupting the flow of the game, and uploads the shot data for analytics and review online, and wherein all information related to a given user are reviewable by an authorized coach user through a web-based coach access account. The system is further operable to provide the coach user rights for providing corrective or instructive feedback to the user, including visual recommendations such as modified target areas.

20 Claims, 35 Drawing Sheets

Related U.S. Application Data continuation of application No. 14/265,218, filed on Apr. 29, 2014, now Pat. No. 9,295,895, which is a continuation-in-part of application No. 12/501,106, filed on Jul. 10, 2009, now abandoned, which is a continuation-in-part of application No. 12/012,942, filed on Feb. 6, 2008, now Pat. No. 8,708,841, which is a continuation-in-part of application No. 12/012,943, filed on Feb. 6, 2008, now abandoned.

(60) Provisional application No. 61/134,670, filed on Jul. 12, 2008, provisional application No. 60/899,913, filed on Feb. 7, 2007, provisional application No. 60/899,914, filed on Feb. 7, 2007.

(51) Int. Cl.
    *A63B 24/00*   (2006.01)
    *G09B 19/00*   (2006.01)
    *G01S 19/19*   (2010.01)
    *G06F 19/00*   (2018.01)
    *A63B 102/32*  (2015.01)
    *G16H 20/30*   (2018.01)

(52) U.S. Cl.
    CPC ....... *A63B 2220/70* (2013.01); *A63B 2225/20* (2013.01); *A63B 2225/50* (2013.01); *G01S 19/19* (2013.01); *G06F 19/3481* (2013.01); *G16H 20/30* (2018.01)

(56) References Cited

U.S. PATENT DOCUMENTS

| | | |
|---|---|---|
| 5,882,269 A | 3/1999 | Lewis |
| 6,236,360 B1 | 5/2001 | Rudow et al. |
| 6,322,455 B1 | 11/2001 | Howey |
| 6,456,938 B1 | 9/2002 | Barnard |
| 7,010,550 B2 | 3/2006 | Tarlie |
| 7,118,498 B2 | 10/2006 | Meadows et al. |
| 8,708,841 B2 | 4/2014 | Doherty et al. |
| 9,295,895 B2 | 3/2016 | Doherty et al. |
| 2002/0010544 A1 | 1/2002 | Rudow et al. |
| 2002/0072815 A1 | 6/2002 | McDonough et al. |
| 2003/0191547 A1 | 10/2003 | Morse |
| 2004/0147329 A1 | 7/2004 | Meadows et al. |
| 2004/0172284 A1 | 9/2004 | Sullivan et al. |
| 2004/0180709 A1 | 9/2004 | Takahashi et al. |
| 2006/0114363 A1 | 6/2006 | Kang et al. |
| 2006/0212221 A1 | 9/2006 | Liu |
| 2007/0026958 A1 | 2/2007 | Barasch et al. |
| 2008/0108456 A1 | 5/2008 | Bonito |
| 2008/0201107 A1 | 8/2008 | Doherty et al. |
| 2009/0233735 A1* | 9/2009 | Savarese ............ A63B 71/0669 473/407 |
| 2010/0009780 A1 | 1/2010 | Doherty et al. |
| 2015/0126308 A1* | 5/2015 | Penn .................... A63B 69/36 473/407 |
| 2016/0199694 A1 | 7/2016 | Doherty et al. |

OTHER PUBLICATIONS

Global Positioning System, Wikipedia, http://en.wikipedia.org/wiki/Global_Positioning_System.

Pelz, Dave, "Master Awkward-Distance Pitch Shots," Dec. 1, 2006, retrieved from URL http://www.golf.com/instruction/master-awkward-distance-pitch-shots on Jun. 18, 2014.

Tally, S., New GPS standards won't affect precision farming, Purdue News, http://www.purdue.edu/uns/ html4ever/0007.Morgan.GPS.html.

U.S. Appl. No. 60/899,914, filed Feb. 7, 2007 Specification & Drawings.

U.S. Appl. No. 60/899,913, filed Feb. 7, 2007, Specification.

U.S. Appl. No. 61/134,670, filed Jul. 12, 2008, Specification, Claims, Drawings.

* cited by examiner

COACHING AID FOR GOLF

CROSS-REFERENCE TO RELATED INVENTIONS

This application is a continuation of U.S. application Ser. No. 15/079,086, filed Mar. 24, 2016, which is a continuation of U.S. application Ser. No. 14/265,218, filed Apr. 29, 2014, now U.S. Pat. No. 9,295,895, which is a continuation-in-part of U.S. application Ser. No. 12/012,942, filed Feb. 6, 2008, now U.S. Pat. No. 8,708,841, which claims the benefit of U.S. Provisional Application No. 60/899,914, filed Feb. 7, 2007, each of which is hereby incorporated by reference in its entirety. U.S. application Ser. No. 14/265,218 is also a continuation-in-part of U.S. application Ser. No. 12/012,943, filed Feb. 6, 2008, which claims the benefit of U.S. Provisional Application No. 60/899,913, filed Feb. 7, 2007, each of which is hereby incorporated by reference in its entirety. U.S. application Ser. No. 14/265,218 is also a continuation-in-part of U.S. application Ser. No. 12/501,106, filed Jul. 10, 2009, which claims the benefit of U.S. Provisional Application No. 61/134,670, filed Jul. 12, 2008, each of which is hereby incorporated by reference in its entirety.

BACKGROUND OF THE INVENTION

1. Field of the Invention

The present invention relates generally to systems and methods for tracking and improving golf performance using statistical analysis of actual performance versus targets.

2. Description of the Prior Art

Prior art diagrammatic views of golf performance are known, specifically directional and distance information is known to be generated based upon a golfer's performance on a specific course of play. Also, generally, golf performance statistical programs are known, in particular for using GPS coordinates for tracking shot distances from a starting point, such as a tee, to an end point, such as the hole on the green of a golf course. However, detailed analytics that are specific to course conditions, historical play and trends, targets, and multiple player statuses have not been included. Thus there remains a need for systems and methods that provide for improved statistical analytics of golf performance that includes image-based outputs. Moreover, there remains a need for a portable, printed pocket-sized version of shot performance for an individual golfer based upon a specific club and golf course situations, past performance and targets, along with statistical likelihood for present performance under the same or similar conditions.

Additionally, traditional coaching is typically provided during live sessions in a one-on-one or in a group settings, or through interactive play simulations, wherein a coach can review the live performance of the student(s). There is a lack of capacity to track, monitor, and provide guidance based on play on natural course conditions. Thus there remains a need for systems and methods that provide for improved statistical analytics of golf performance and that include graphic and image-based outputs based on golfer trends upon actual golf play on course situations, wherein the golf play is reviewable by a coach or teacher for third party student(s).

SUMMARY OF THE INVENTION

In a preferred embodiment, the interactive golfing system includes a portable device operable for communication through a network to at least one remote computing device, wherein a user inputs, during and/or before a round of play, shot, setting and target information which is communicable to the remote device(s). Further, the inputs may include or correlate to GPS information and be stored in a local and/or remote historical database, the inputs and historical information able to be analyzed locally and/or remotely.

Aspects of the present invention are to provide golf performance analytics, including shot zone diagrams and target analytics, to assist with identification and understanding of golfer errors and trends so that adjustments to form, strategy, and ultimately performance can be made.

Another aspect of the invention is to provide shot zone diagrams in a portable, printed pocket-sized version for individual golfers based upon specific clubs, target, golf course situations and past performance, along with statistical likelihood for present performance under the same or similar conditions.

Another aspect of the present invention is to provide a system for golf performance analytics wherein a user inputs a series of corresponding starting points and targets, wherein the statistical analysis includes text, tabular, diagrammatic, and/or image-based outputs.

Another aspect of the invention, is to provide analytics whereby the directionality of any shot is to be uniformly and consistently oriented to provide a zeroed-out orientation for each shot, and wherein the shot zone diagrams provide information including targets, trends in the user's golf performance over a predetermined period, shot misdirection and corresponding causes related thereto, and/or providing a portable printed version of past or recommended shot performances for any given golf club, golf course, or conditions.

In one aspect of the invention an interactive system is provided for interaction with a third party, e.g., a coach or teacher, who can provide recommendations, instructive feedback and visual advice such as modified targets, accessible through the interactive device before and/or during golf play. In one aspect of the invention all information related to a given user can be stored locally on the device or remotely on a server or database, each of which may be accessible through a web-based account.

Thus, the present invention provides automatic analytics for user-provided inputs of golf performance over a period of time, including starting points and targets as the user plays a round of golf. Advantageously, compared with prior art, the present invention provides a significant level of detail and customization by the user so that the feedback or statistical output on golf performance and trends provides normalized information that is actionable by the user and/or a third party to correct or improve the user's golf game.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIGS. 12-31 are screenshot images of user interfaces for entering information and viewing analytical outputs according to the present invention.

DETAILED DESCRIPTION

Figure 1:
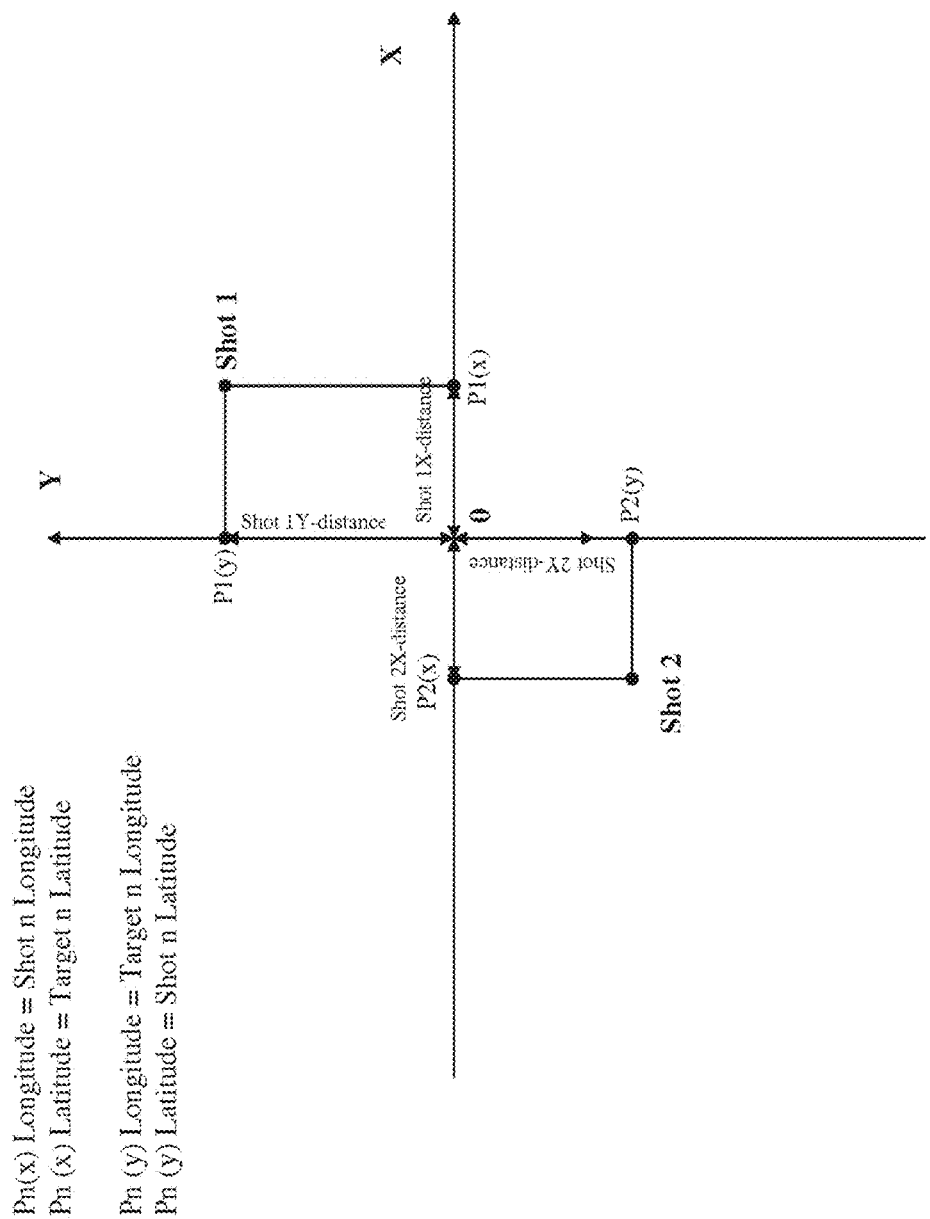
FIGS. 1-11 are schematic drawings illustrating diagrammatic representation of golf performance analytics in accordance with an embodiment of the present invention.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms. Referring to the drawings in general, the illustrations are provided for the purpose of describing a preferred embodiment of the invention and are not intended to limit the invention thereto.

The present invention provides a system for golf performance analytics using a computer system including a mobile computing device for receiving inputs from a user during golf play. Golf play may include playing golf, whether a single shot or a series of shots, on the holes of a golf course, a practice tee, or any other location where a golfer may make at least one golf shot. Golf shots include taking a shot from a starting point towards an optionally designated target, the golf shot resting at a ball location. Typically, in a series of golf shots, the ball location becomes the starting point of the subsequent golf shot. Various configurations of the computer system and mobile computing device are described infra.

Input Mechanisms.

Users, including golfers, coaches, teachers or another third party, input information related to golf play into the device using at least one input mechanism, including, but not limited to, a touchscreen incorporated into the graphic user interface (GUI) or display and operable with a human hand or stylus, functional and activatable components such as keys, buttons or joysticks, on screen keyboards, voice or movement recognition technology, or any other input mechanisms known to one skilled in the art. In one embodiment, the GUI or display is a touchscreen that is activatable by a user's finger or a stylus to input information, whether by points, lines, drag-and-drop motions or other styles or uses known in the art. In another embodiment the input mechanism may be external to the device but connected, either wired or wirelessly, to the device through an input/output controller.

During golf play, at least one user may input information via the at least one input mechanism. Input information includes information relating to making at least one golf shot and course, weather and/or user conditions. Golf shot information includes at least one starting point and, optionally, at least one target, which may be pinpoint locations, multi-dimensional areas, or zones on the fairway, green or other features of a golf play landscape. Each starting point and target may be represented by at least one visual representation on the GUI or display. Furthermore, the GUI or display may include additional visual representations such as golf play landscape features and analytics indicators. In one embodiment the GUI or display may provide interactive features and advertisements, either through the network or from instructions stored on the mobile device.

Preferably, the mobile device includes global positioning satellite (GPS) functionality, enabling user inputs, through the at least one input mechanism, to be combined with at least one GPS coordinate and stored with, or in replacement of, the user input. For example, a user input of a starting point through the touch of a golf hole visual representation on a touch-interactive screen would be graphically represented on the screen and stored in memory in combination with a GPS coordinate representing the location of the starting point. While GPS coordinates are not absolutely precise in their representation of a ball's starting point position on Earth, the GPS coordinate stored in memory is itself an absolute and infinitely precise representation of a location within the mobile device's virtual system, as coordinates that are zero-dimension, geometric point, locational representations. In one embodiment of the present invention the GPS coordinates are generated using an ASP.NET library for the GPS calculations, for example as with Geo Frameworks. For calculation of distances between two GPS coordinates using the ASP.NET library, the Position class is used. Two instances of Position class are initiated with longitude and latitude that they get from the handheld GPS device, those positions are the start and result coordinates. The Position.DistanceTo (Position destination) method is used to obtain the distance between two points. Alternatively, the present invention systems and methods are adaptable to be used or retrofitted to use on existing GPS mobile devices.

User Inputs.

During or before a first golf play, according to one embodiment of the present invention, a user enters a unique user identification and secure login, such as by password, via the device interface, thereby creating a user account. The system and methods of the present invention also provide for options that permit a golfer to set up pre-game settings including starting points, targets and default targets for a particular golf course. For example, a user may choose to play from the white tees, so that the first starting point on each hole of a golf course may be defined, and additionally choose to apply default targets to some holes and new targets to other holes, to account for the weather or golfer conditions. Favorite clubs can also be set up, which prevents users from having to scroll through the entire list of clubs when reviewing shots on the user interface. Secondary shot information may also be saved in the pregame settings. All pre-game settings, once inputted, are easily retrievable and allow the user to save time when playing a game. In addition, pre-game settings can be modified as needed by the user during the course of play.

Shot Information.

Before making a first shot during golf play, a user inputs primary shot information, including at least one starting point representing the location of the golf ball before a golf shot. In another embodiment, the user additionally inputs a target. Each primary shot input is associated with GPS coordinate data or relational data, whether in a GPS virtual system or a stored relational location system, respectfully. In another embodiment, during the golf play of a hole on a golf course, the user inputs a series of starting points and targets, including an initial start point and target for a first golf shot, an intermediate start point and target for a second golf shot, and at least another start point and target for a third golf shot, until the golfer successfully reaches the golf hole. In one embodiment, the starting point and target relate to a golf course, and more particularly to a hole playable on a golf course. In another embodiment, the starting point and target relate to a landscape used for practice, and the user is a third party entering information relating to a golfer's shot. Additional combinations are apparent to those skilled in the art upon a reading of the foregoing description.

In another embodiment of the present invention, the device prompts the user to mark the starting point by either recording the user's position or permitting the user to input the starting point via the interface using an input mechanism.

The device may further prompts the user to input a target, such as by prompting whether the pin that marks the hole is to be used, whether the default target is to be used or modified, and/or whether a new target is to be inputted. In one embodiment the user may ignore the target prompt altogether, thereby using the default target by default. In one embodiment, if the user enters YES, and the pin location or default target is to be the target, then the user proceeds with the shot to hit the target; if the user enters NO, then the user modifies the default target, enters a new target altogether, or refuses to use a target.

Once a shot is completed and the ball lands in a next location or position, the ball location is inputted by the user and is typically used as the starting point for the next shot, except in circumstances described infra, such as shots out of bounds and shots in hazards, such as water. The user may choose to continue until the target is reached or new target(s) corresponding to any additional starting point(s). For a hole on a golf course, the user continues until the hole is played out, and the ball is placed in the hole. The user continues to mark the pin or next start location and a series of start-to-target entries are made until the hole is played out, including putts.

A starting position or resting ball location is inputted by a user via the input mechanisms to mark the user's ball location as a pinpoint position, the resting ball position being the resting position of the previous shot and the starting position of the upcoming shot. The starting position may be inputted by capturing the device's location, when a user is standing near or over the ball location, or may be inputted through selection of a point on the GUI or display, which may be related and stored with associated GPS coordinates or relational position information.

Additionally, secondary shot information may be inputted by a user, including a club selection, golf course conditions, weather conditions, golfer conditions, equipment specifics, shot corrections, penalty shot positions, and combinations thereof. Secondary shot information may be entered for each shot or at least one shot. Further, a user may enter secondary information on one shot and choose to have the secondary information serve as default secondary information, wherein the default secondary information is automatically entered for each consecutive shot unless otherwise directed by the user. One, some or all of the secondary information may be set as default when the user inputs the pre-game settings or may be set as default during golf play, such that the secondary information may be modified from its default setting at any point during golf play.

Targets.

A user enters at least one target as a pinpoint coordinate location, a multi-dimensional area or a zone on the fairway, green or another feature of a golf play landscape. The user may enter targets before, during or after golf play. Targets may be intermediate targets en route to a final target. Final targets may be pinpoint locations, such as a pin location.

Target points are zero-dimensional, single pinpoint coordinate locations on the golf play landscape and are inputted by a user. Target points are entered using an input mechanism via the device interface and correspond to a GPS or relational position. An exemplar target point is a golf course hole coordinate location.

Target areas are areas located on the golf play landscape. In one embodiment, a target area is defined by its position, dimensions and shape, as inputted by the user via an input mechanism; the target position defines the center of a target shape, and the target dimensions define the dimensions of the target shape. Such a target area may be defined by choosing a target position, then selecting a predetermined target area shape from a drop-down list, wherein the device automatically retrieves target dimensions from the default pre-game settings or from historical data from a user account. Historical data from a user account may include any inputted primary or secondary data, and any corresponding analytics or averages over periods of time, courses, or conditions, such that a target area's position, dimension and/or shape may be uniquely related to a user's golf history. For example, and not as a limitation, an automatically created target area may be created wherein the target position is equal to the average of the inputted club's average distance for the user under the current course conditions (high winds, sunny, healthy golfer), the target dimensions correspond to the percent error indicator (PEI) for the selected club, and the target shape corresponds to the average distance and direction when a target is missed by the selected club.

Notably, any target, whether a point, area or zone, may be automatically recommended based on an account's historical data and pre-game or default settings. For example, all historical data associated with a selected club may be combined with a default setting that all targets are points or zones in order to automatically calculate the position of the point or the area of the zone. An automatically calculated target may appear on the graphic user interface for viewing by the user, who may modify the target or save the target as a default target, if so desired. In one embodiment a target area may be calculated using historical club data for an account, wherein the target position is equal to distance from the starting point, centered on a fairway or green, equal to a club average for the account over a particular time range. Alternatively, the position distance from the starting point may be equal to the club average plus or minus a percentage of the club average. The target shape may be set during pre-game settings using a default, may be calculated using statistical analysis similar to FIGS. 32-33, or may be inputted by the user. The target dimension(s) may be equal to a percentage of a club average for the account over a particular range, the percentage either being inputted during play or before play as a default in the pre-game settings. For example, a user may input the target position to be 5% above the club average, the target dimension range to be within 15% of the club average, the target dimension width to be within 25% of the club average, and the target shape to be an oval. Further, any averages may also account for other primary or secondary shot inputs, such that the target calculation may be limited to historical information for the account, or multiple accounts, matching the course condition, lie, shot type, starting position, etc.

Alternatively, the target area may be defined by selecting a target point, selecting a predetermined target shape, then inputting at least one dimension for the predetermined target shape; the system may automatically calculate other dimensions if only one dimension is inputted, and the device may automatically draw the target area defined by the user with the target point as the center of the target area. To speed the play of golf, a user may input any of a target, a target position, at least one target dimension, a target shape, and/or a target outline before play during the pre-game settings, during play, during play and set as a default, or after play for future use or account modification.

In another embodiment a target area is defined by customized outline created using the input mechanism, such that the outline consists of a series of GPS or relational position points defining the border of the target area. In such an embodiment, a user may use their digits or a stylus to demarcate an outline of the target via a touchscreen, either point-by-point, segment-by-segment continuous lines, or by a single continuous line. In another embodiment, a user may further customize target areas by choosing to limit the target's outline within the fairway, the result being for a target square of 50 yards in length being placed on a fairway of 40 yards in width to be automatically modified such that the width of the square is 40 yards up to the fairway's borders, yet the length remains 50 yards. Similar customizations may be made with respect to a green, practice area, or other golf play landscape feature.

An example, but not a limitation, includes a user, before golf play, defining all targets as being an oval having a width of 25 yards and a depth of 15 yards, such that, during golf play, the user simply inputs a target area position on the GUI or display, the device automatically defining an 25 yard by 15 yard oval with the inputted position as the oval's centerpoint. As another example, the user may set pre-game defaults as including a custom outline as the default target for hole 1, an oval with dimensions of 25 yards by 15 yards for hole 2, a circle with a radius dimension of 20 yards up to the fairway border for hole 3, etc.

Target zones are areas that may be defined by a range of distances as a length and a width that stretches to the edges of a feature, such as a fairway, green, landscape border or golf course border. In one embodiment, a user defines the target zone's length as being a range of distances from the starting point (e.g., input of 200-230 yards would create a target zone of 30 yards in length, the zone starting at 200 yards from the starting point and ending at 230 yards from the starting point), and the user defines the target zone's width as being a landscape feature (e.g., the feature being a fairway, thereby creating a target zone stretching between the borders of the fairway, with a 200 and 230 yard arch as the distance dimension borders). In another embodiment, a user may highlight a portion of the fairway that is the desired target zone with a swipe of the finger or using another input mechanism, thereby allowing the device to define a range of distances and feature by estimation, either by the width of the digit being applied or by calculating a swipe center and applying a default range of distances thereto. For example, if the interface receives an input averaging between 280 and 300 yards around the fairway center, the device may prompt the user to confirm such estimation, although the user may, by default, accept such estimation, or the user may modify such estimation.

Targets can be entered before, during or after golf play, in relation to a starting position, golf course hole, and/or landscape. In one embodiment, when targets are entered before golf play, a user enters at least one target, which can be saved in the system's pre-game settings. In such an embodiment, when inputting primary shot information, the system may automatically display and/or input the pre-game target settings, which the user can accept by default, modify or completely replace. In one embodiment, after a target is inputted through at least one input mechanism, the target is displayed on the graphic user interface of the device and the user may save the target as the default target, the default target being automatically displayed and/or inputted whenever the user is at, or near, the same starting position, depending on the pre-game settings.

After the first shot, and in relation to each new starting position, a user may continue to enter new targets as desired. In one embodiment, for each target being inputted, the system may prompt the user to select a club from a club list or automatically displays and/or inputs a default club previously identified by the user, either in the pre-game settings or during previous golf play. In another embodiment, once a club is selected, the system prompts the user with a target recommendation based on the golfer's history using the selected club; subsequently the user either approves or removes the target recommendation, modifies it, or replaces it with a new target. In one embodiment, if the user selects a lie of "green", the next shots on that hole will automatically default to green, and the club will automatically change to putter; such a feature, as with most features of the invention, are designed to save the user time when playing and/or reviewing a round.

Notably, the analytics based on target areas and zones may use any number of distance measurements, whether it be to the nearest point on a target outline, the point where the outline intersects with a line connecting the starting position and the target center, the target center, or another target point. Additionally, a user may simply input a target through an input mechanism with a single click, wherein the single click, without any further inputs, is registered by the device to record the current GPS location as the starting position and to calculate the target using the default or pre-game settings. Such functionality minimizes the device's intrusion into game play by merely allowing a user to slide their hand in their pocket and make a single input before or after making a shot. Alternatively, the device can be equipped with motion sensing technology such that the swing of a golfer is detected, thereby marking the starting location and inputting a target automatically, with no effort during game play on the part of the golfer or user.

Modifications.

In one embodiment of the invention, once a target has been created or selected, a user may modify the target at any time thereafter. Modifications to a target include adjusting the position, dimensions and/or shape of the target, including confining a target zone to a different course feature, or changing whether a target is identified as a default target for a starting point. Target modifications may be made by any user and include modifications made by a coach or third party after golf play, modifications made by a coach during golf play, modifications made by a golfer or user before golf play, or, more generically, modifications made by any user at any time after a target has been created or modified. Target modifications are inputted by a user in the same, or similar, way that a target is first created.

By way of example and not limitation, one embodiment of the invention permits a user to modify a target area location during golf play. Before a user hits the first shot on a par 4, the user can choose to modify a default target due to high winds. By selecting the target area on the GUI or display, the user may input new dimensions, a new position, a new shape, or even change a target area to a target zone or target point. In one embodiment, the user may simply drag the displayed default target to a new position on the GUI or display, thereby modifying the target but not modifying the default target itself.

In another embodiment of the invention, resting ball locations may be modified by a user. This feature can be used when a golfer's shot lands in a body of water, out of bounds, or in a hazard area, wherein a ball location will differ from the subsequent shot starting point. According to typical golf rules, landing in one of these areas requires the golfer to either retake the shot from the previous starting point or drop the ball in a certain location away from the ball location. In such a case, the user may want to input the ball location, even though it is not playable, in order to allow the ball location to be included in the statistical analysis. Additionally, the user may still want to input a starting point that differs from the ball location so that the statistical analysis and other features, such as feedback and default target areas, remain properly applied to the shot location as well. For example, it may not be helpful to consider that the shot merely landed at that drop point, rather than at the actual location or area where the ball hit the water. As with inputting target information, ball locations may be inputted through the interface using any one of the input mechanisms. In one embodiment, the ball location which differs from a starting point will be indicated with an X to indicate that this is an estimate rather than an actual pinpoint location of the ball at the end of that shot.

Once a target is finally inputted, the golfer may proceed with the shot and input the resulting ball location position. By observing the ball location after a shot, and depending on whether the target was accurate or beneficial to the user, the user can choose to save the target as a default target for future use when making a shot from the starting point. The user may also input whether the default target should be used only at that starting point, typically in the case of a tee box, or be used within a certain distance of that starting point, such as a second fairway shot on a par 5. The default target may be saved to the course settings by the user for future play or review by a coach or third party, such as being saved to the course map for review during future play when deciding where to play a target.

Analytics.

The GPS-captured and/or received inputs may be stored locally on the device itself or transferred between devices before, during or after golf play through a wired or wireless network. For example, a user may choose to continuously upload data from device to device during golf play via a wireless network, upload data to a mobile device through a wired connection during golf play, or upload data after golf play to a server device. Various computer system embodiments allow for a plurality of information sharing scenarios over wired and/or wireless networks, as is described supra. These inputs can be associated with one or more user accounts, the user account being that of the golfer, coach, third party, or user inputting the information, such as a caddie.

GPS data may be downloaded from or uploaded to another device, preferably directly from the user device without requiring additional software or data to be saved or otherwise stored on an intermediate computer. While the user is logged online from any connected device, the user may access any presently loaded or prior-loaded inputs from golf play for modification or manipulation, including providing inputs for additional information that provide more detail on the conditions of play. Software may reside on one or many of the computing devices within the system for performing statistical analysis on the inputs and for providing output in the form of text, tables, diagrams, images and combinations thereof. In one embodiment, the data and analytics is stored and categorized by user, golfer, coach, course, hole, primary shot information, secondary shot information and/or course conditions.

In one embodiment, the present invention provides for situational golf shot data and analytics. Significantly, the golf shot data and analytics of the systems and methods of the present invention are provided in a relative mode, i.e., each shot is directionally compared to a starting point and a target, wherein that direction is zeroed out to a (0,0) coordinate starting point and the direction is consistently oriented for each shot such that when all shots are considered collectively, regardless of actual GPS or relational direction or positioning, trends information is quickly identifiable because all shots are aligned in the same direction for the purposes of the analytics on the remote server computer. Thus, while the actual shots may be taken during play on a golf course, the situation-neutral based system eliminates the actual GPS directionality of any shot from start point to target and uses a zeroed directionality instead to facilitate comparison of shots and their deviation from target direction.

The systems and methods of such an embodiment are thus particularly useful in a practice mode. Since the directionality is zeroed by the software running on the server computer, the inputs from the application user and GPS data provide accuracy of the actual shot versus target comparisons, but the data is also useful for practice apart from the context of a course. The situational shot data, or situation-neutral shot data, is based upon the initial start point and first target; the second start point and second target, etc., until the final shot from final start point to final target (and final actual shot) are completed, wherein each respective start point and target are considered out of context of a course of play or golf course location. Each shot start is zeroed out and its location established as the zero point with direction of play oriented to a consistent, predetermined direction, such as true north. Statistical analytics relating to the user's shot data are provided including outputs having scattergraph diagrams that include information relating to the directionality of any shot to be uniformly and consistently oriented to provide a zeroed-out orientation for each shot, thereby assisting the user/golfer with identification and understanding of errors and trends related to shot misdirection and the corresponding causes related thereto. In this way, adjustments to form, strategy, and ultimately performance, can be made by the user.

The inputs, or a selection thereof, captured during golf play, can be transformed into at least one graphical visual representation of the starting point and target and further including analytics indicators for shot accuracy based upon user inputs for the target for a multiplicity of shots. Other options available to the user include saving inputs based on the visual representation itself, operating a report function to generate basic feedback to the user about his/her play inputs compared to targets, clubs, conditions, and combinations thereof. Reports can include average score, breakdown by par/hole, scrambling percentage, sand saves, driving accuracy, and other standard metrics and combinations thereof, as well as trends information. Additionally, information is available for review by club, by conditions or situations such as represented by the secondary inputs. A percent error index (PEI) is also available; this PEI is a calculation of how close the actual user shots were from start to targets for each series within the play period, which may be the golf course, a series of holes on a golf course, a practice session, a golf school or lessons by professional instruction over a predetermined period of time.

FIGS. 1-11 are schematic drawings illustrating diagrammatic representation of golf performance analytics in accordance with an embodiment of the present invention.

FIGS. 12-31 illustrate screen shot images of user interfaces for user input of information and coordinate data and for viewing statistical and analytical outputs.

Figure 16:
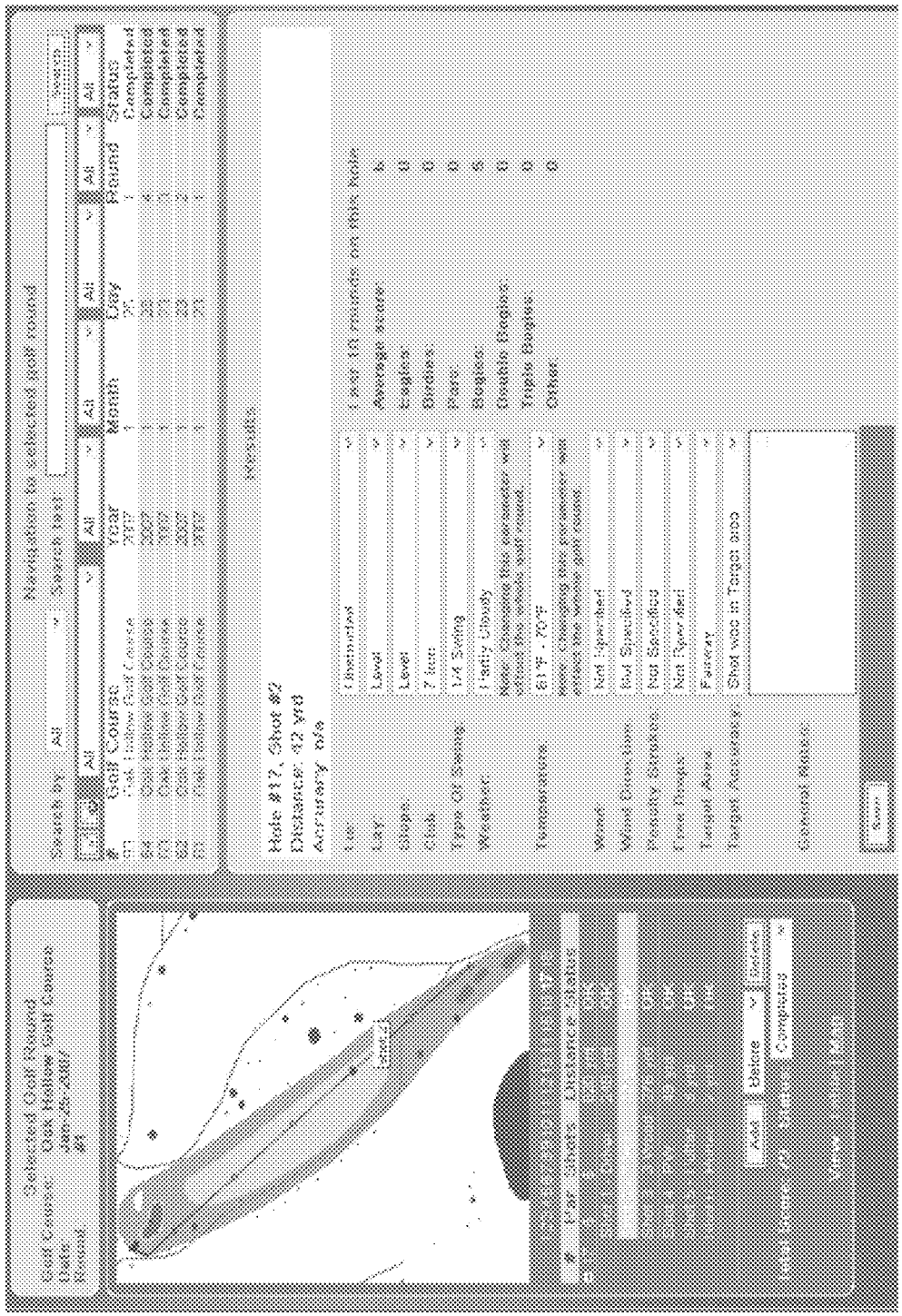

In one embodiment of the present invention, the systems and methods provide for at least two different ways to look at or review a round with visual representations via the website interface, specifically "Table" and "Map" views, as illustrated in the figures. Table view is an easy to view screen that just lists each shot, along with the distance, as illustrated by the website screen shot in FIG. 15. A Map view is illustrated in FIG. 16. To edit the properties of a particular shot, a user simply has to click-select or otherwise indicate or select a given shot represented on the user interface. The user can add secondary shot and other situational information through the user interface. The use of defaults during pre-game settings is preferable so as not to interrupt or slow the flow of the golf game while it is in progress. However, if a device is being used by a third party, such as a caddie, then additional inputs may be made easily with interrupting the flow of the game.

Another option for reviewing a golf round is with the Map view user interface, as shown in FIG. 16. This graphical representation of a golf course is provided for golf course play where those courses have been mapped by a GPS coordinate system, aerially, or otherwise depicted approximately to scale or at least representative of the course layout and distances with respect to each hole. If the course the user is reviewing does not have a map available for any reason, then a blank screen may be provided that indicates that the course is not mapped or that a map is not yet available.

A user may review shots at any time by clicking on the shots below the map, the interface indicating the resting ball location and target for each shot selected. The graphical representation of the shot itself may take any number of forms, including a straight line between the starting point and resting ball location or a curved line to best depict the shot type. Preferably, the user sees the actual line that his/her shots have taken, from the tee to the hole, and/or intermediate shots therebetween.

In the contingency for penalty shots, if a user hits his/her shot into the water, they can't stand next the ball and mark the location with the device. The system allows the user to click on the map to show where a particular shot landed. If no map exists, the user can estimate the distance. The user will go through each shot. When finished the round changes to "Completed" status, and is now part of the statistics in the Reports section (see FIG. 16).

Reports.

Figure 17:
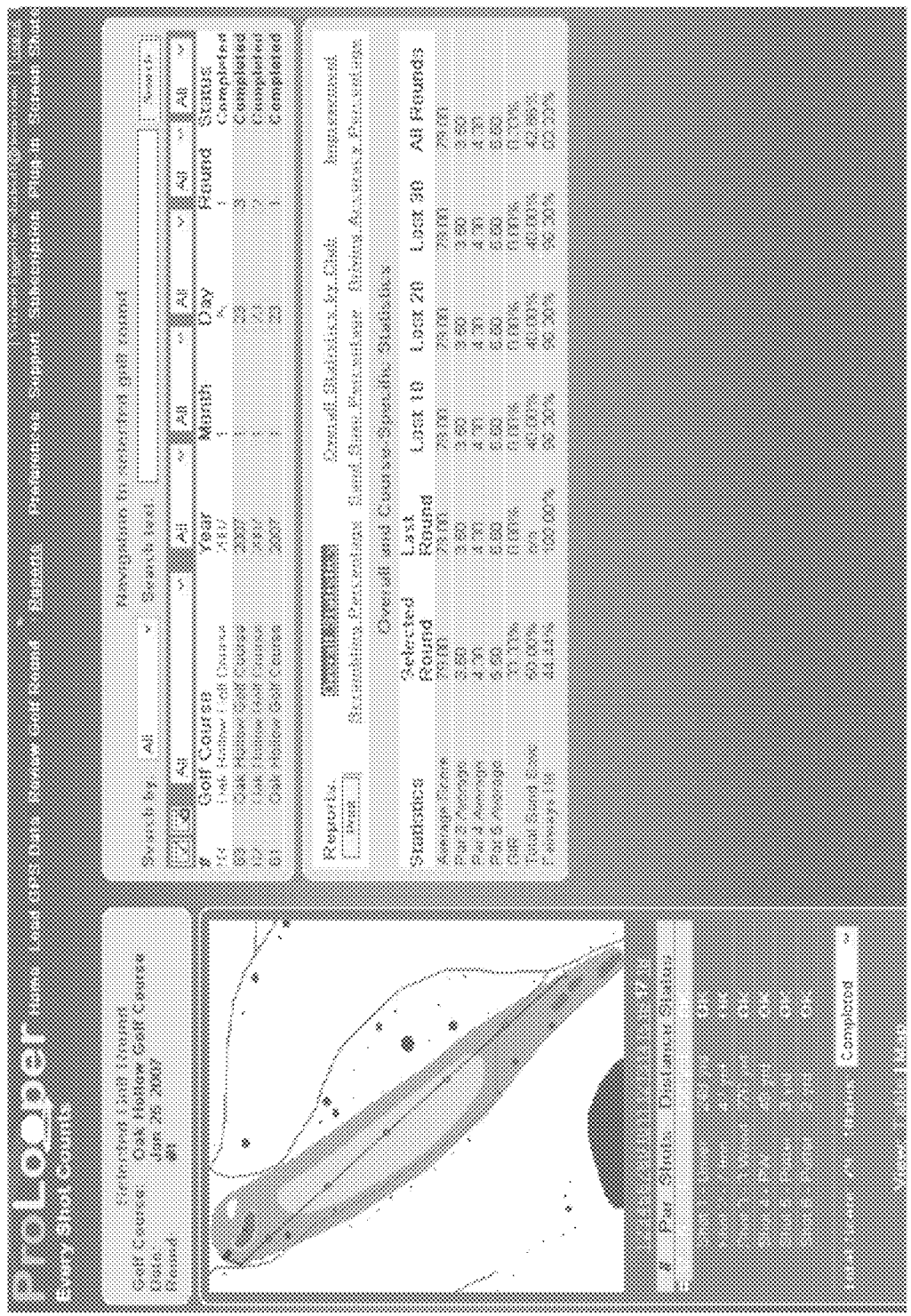

The first report is the Overall Statistics mode. It shows the selected round (you can select any one round from your entire history), the last round, then the past 10, 20, 30, and all rounds to the right. It shows stats for score, average score on the various pars, greens in regulation (GIR), sand save percentage, and driving accuracy percentage. The Reports section, as illustrated in FIG. 17, also allows a user to filter only the rounds they want to see. If the user wants to view only rounds at a particular course, they can select that course from a drop-down menu (filter button). Year, month, and day filters also exist.

Figure 18:
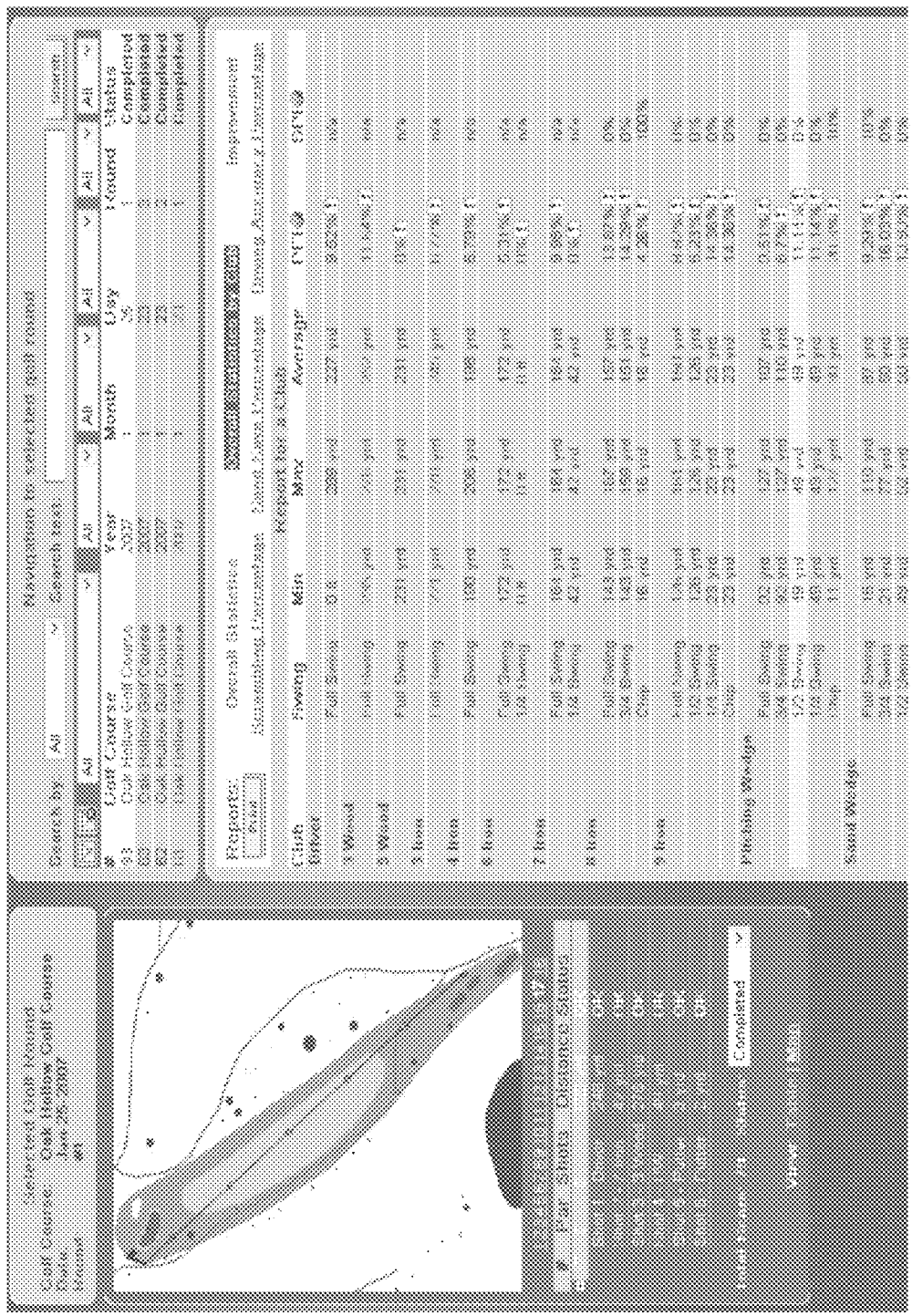

FIG. 18 provides a screen shot view showing an Overall Statistics by Club report. It shows the minimum, maximum, and average distances for each club (and type of swing) that you've used. The PEI (Percentage Error Index) shows you how far you're missing your target by. For example, if I have 100 yards to the pin, and I hit my shot 10 yards away, my PEI is 10%. SPI (Scoring Percentage Index) is a percentage of how often you hit a shot to within 6 feet of the hole.

Figure 19:
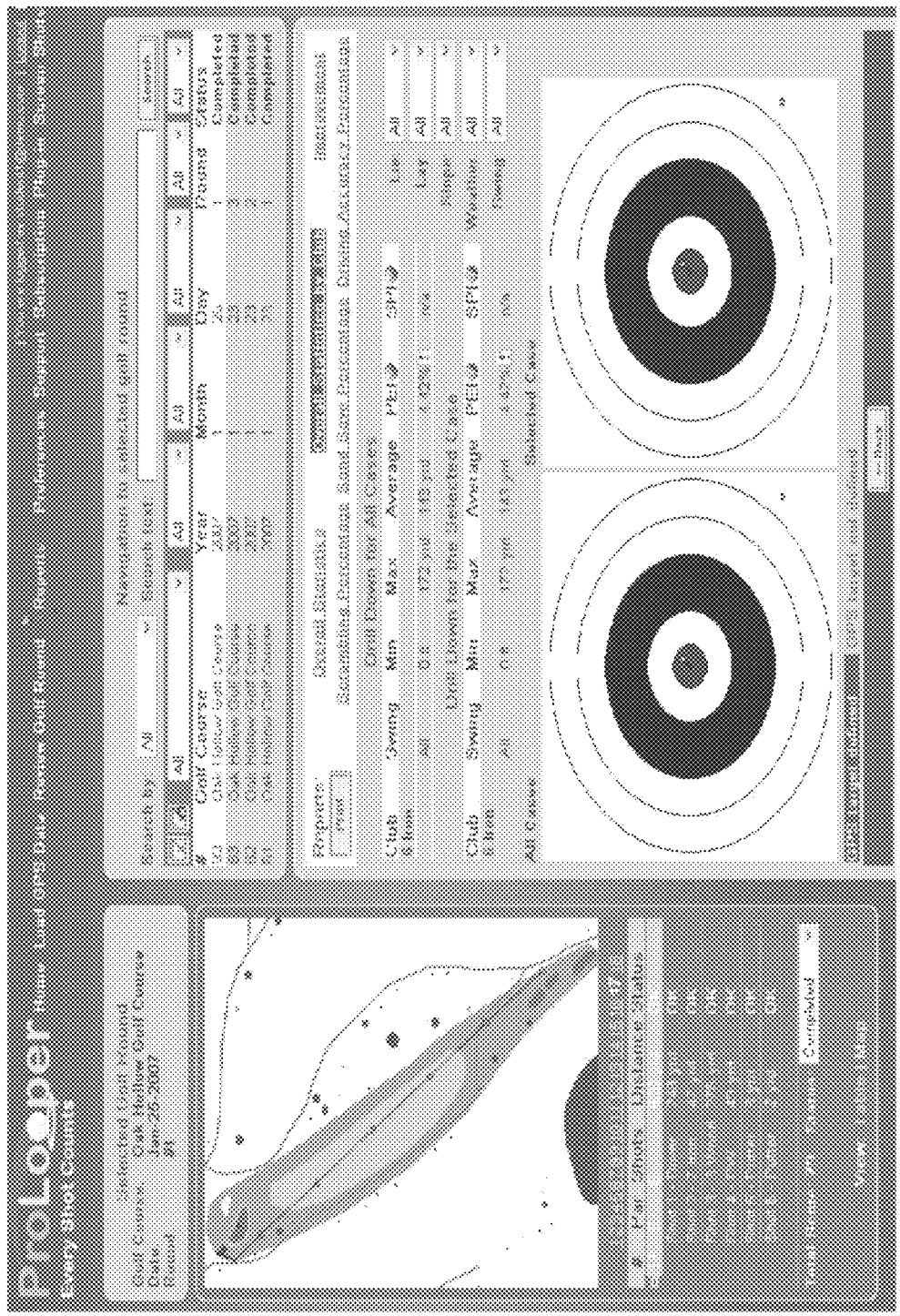

From the same report, as illustrated in FIG. 19, a user can get a closer look at data relating to the accuracy of each club by clicking the club. The first screen that you see below shows you how accurate you are with that particular club, in relationship to the flagstick. Only shots that have a target of "Flagstick" will show here. The left chart is for all shots with that club. The right chart can be further dialed down by clicking the drop-down boxes on the right side of the screen. If you only want to see only those shots out of a fairway bunker, off an uphill lie, out of heavy rough, etc., then the user can specify that at this point.

Figure 20:
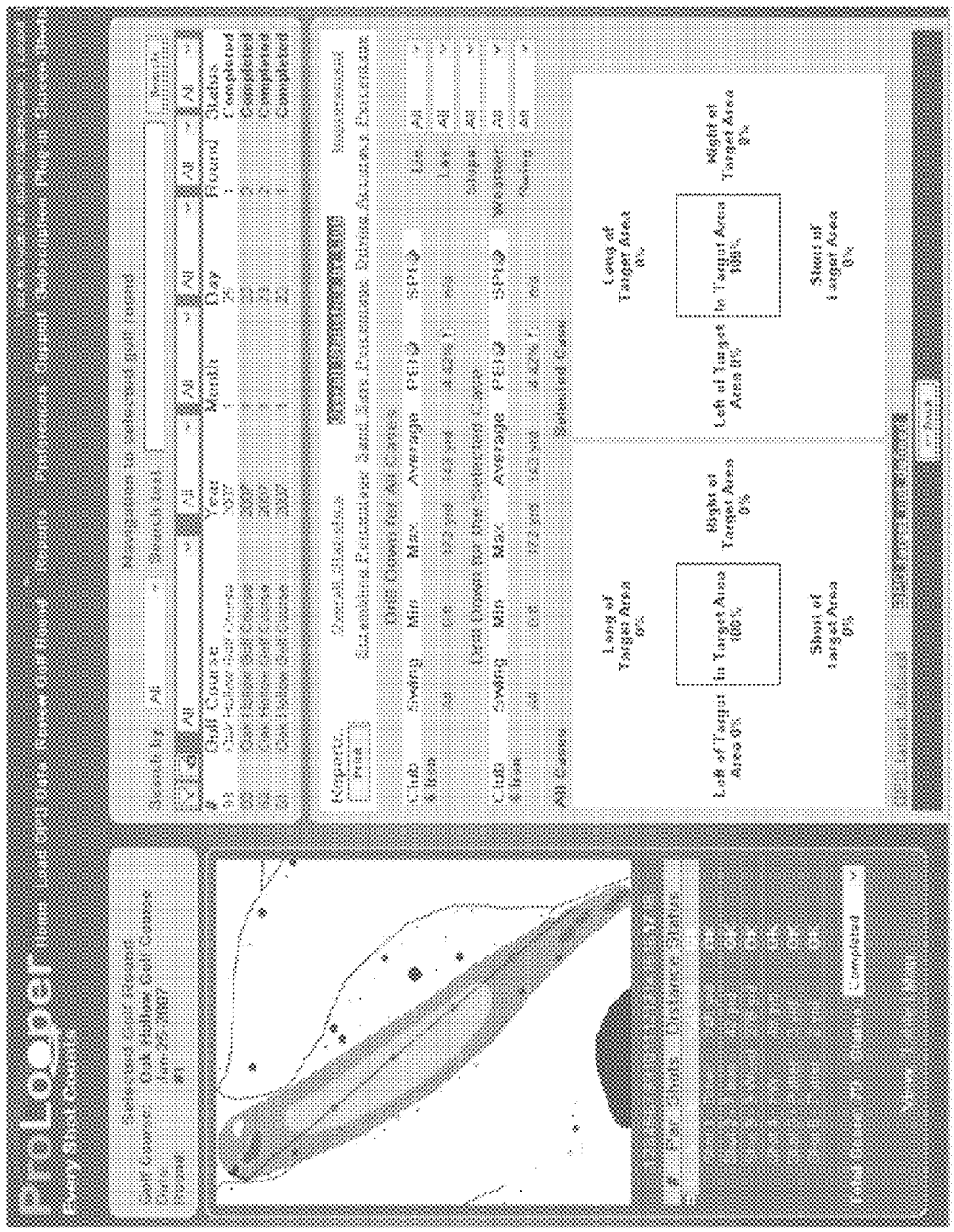

For those shots that are not targeted at a point, the present invention has provided a label for it indicating a "Target Area" or "Target Zone." By clicking the link below the charts as illustrated in FIG. 20 that is labeled "GPS target not defined," the user will see the indicated user interface and graphics. Targets may be inputted as described supra. Same goes for the left chart showing all shots for that club, and the right being selectable. Shot information with a particular club may be stored and referred to later on when providing target recommendations to the user when he selects the same club on the same course in the future.

Figure 21:
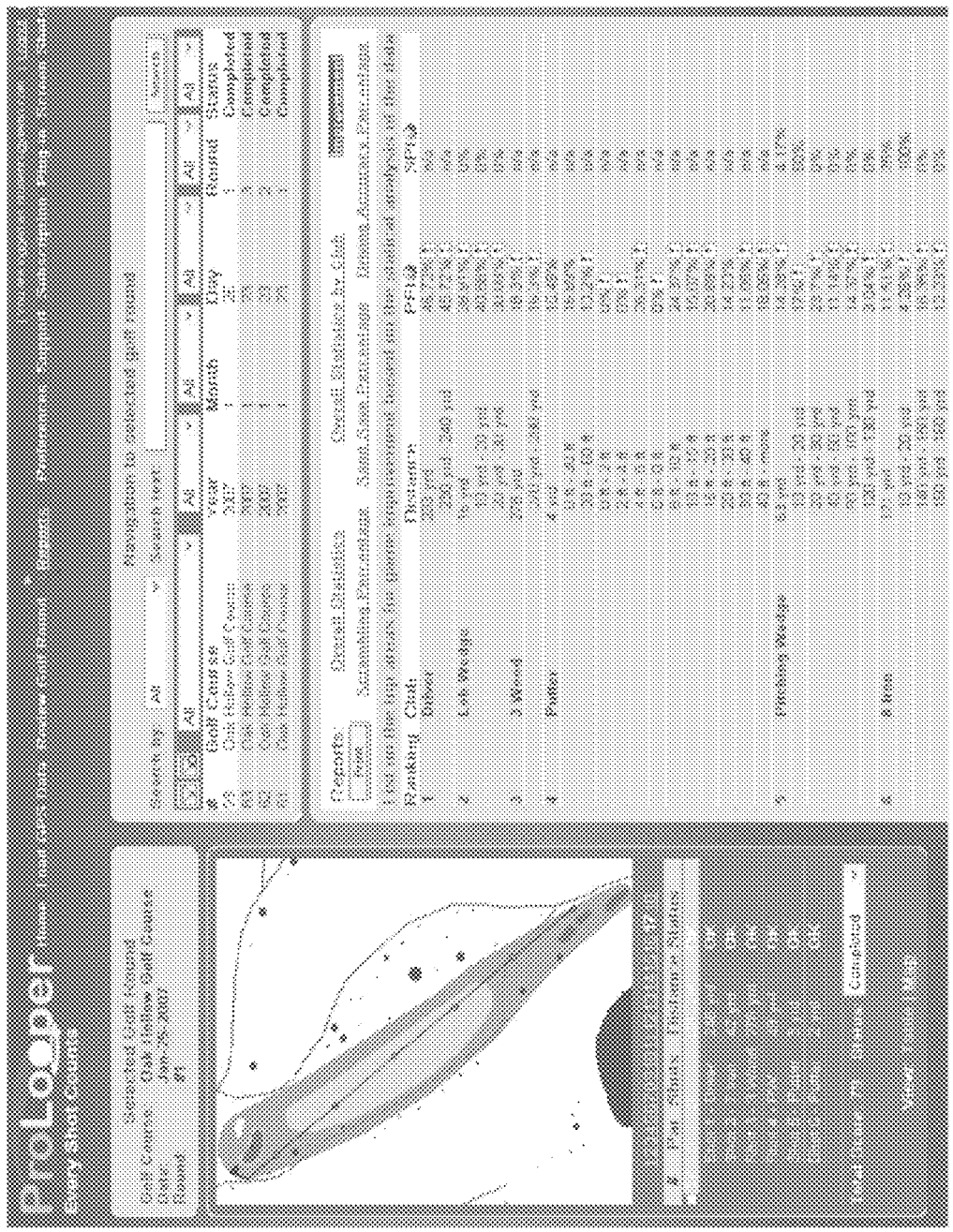

The next report shown in FIG. 21 is the Improvement report. This shows a list of clubs, with the clubs that have the highest error percentage at the top. The higher the PEI, the worse the user is with that particular club. Those are the clubs with which the user needs to work on improvements.

Figure 22:
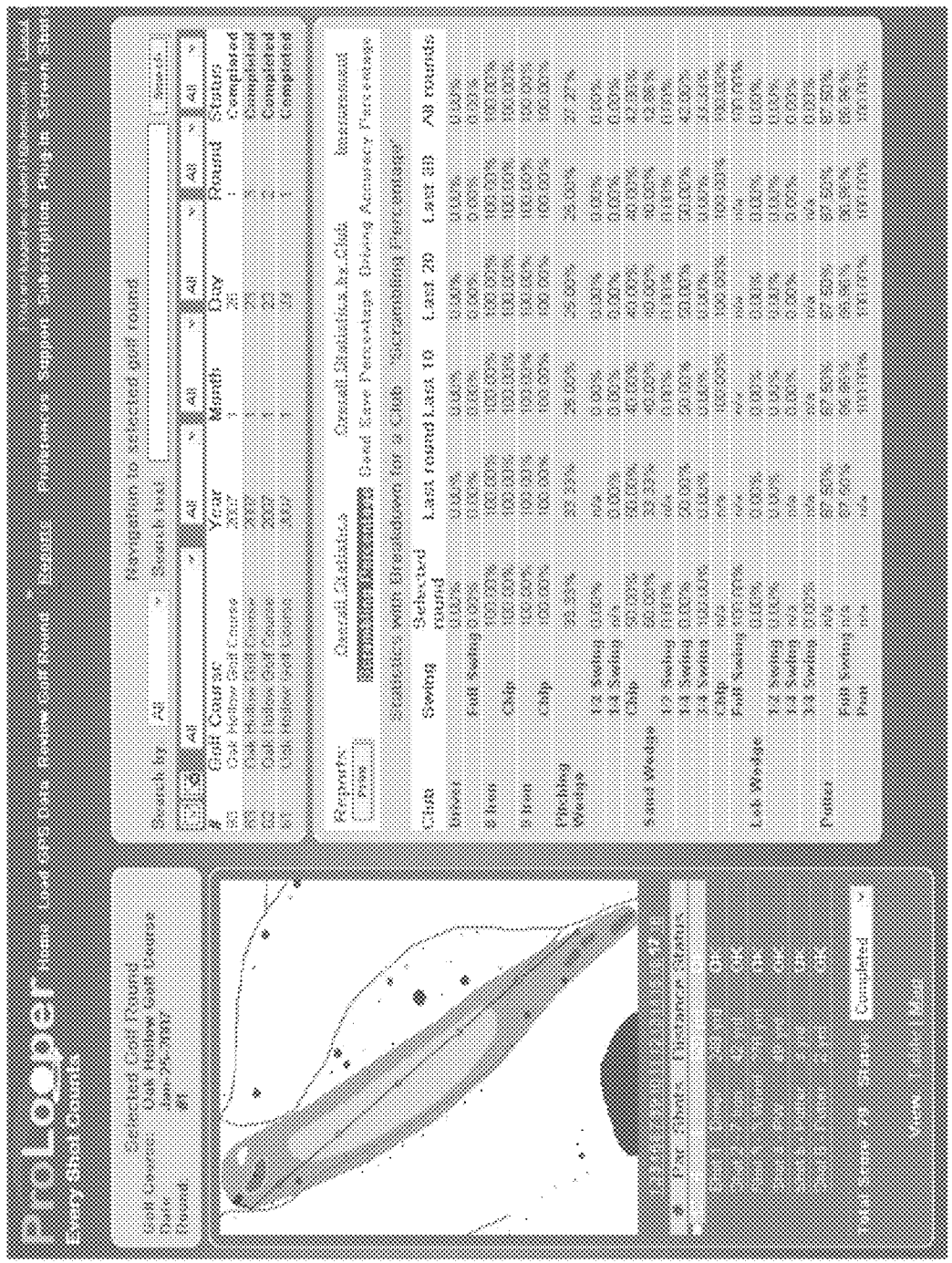
Figure 23:
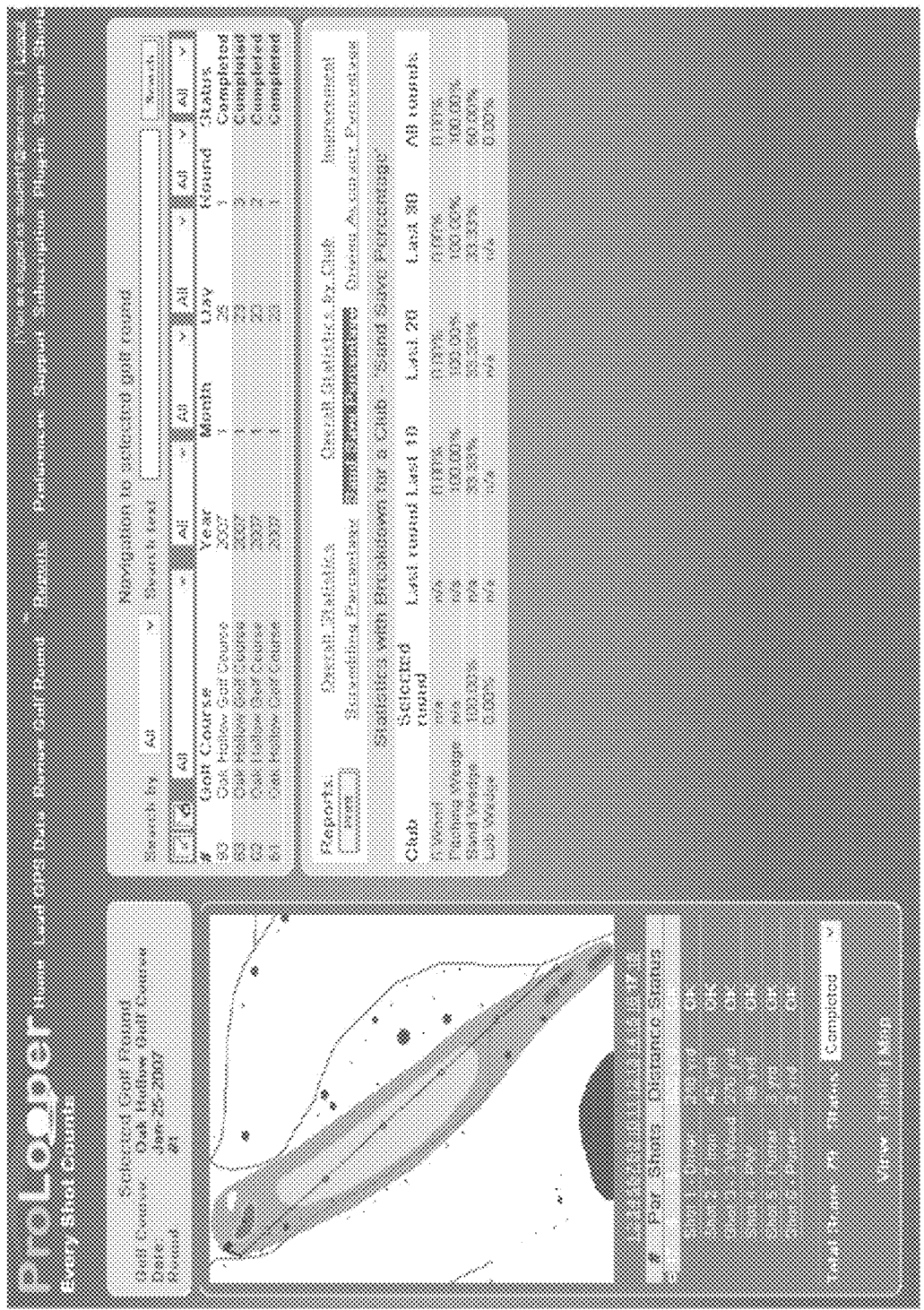
Figure 24:
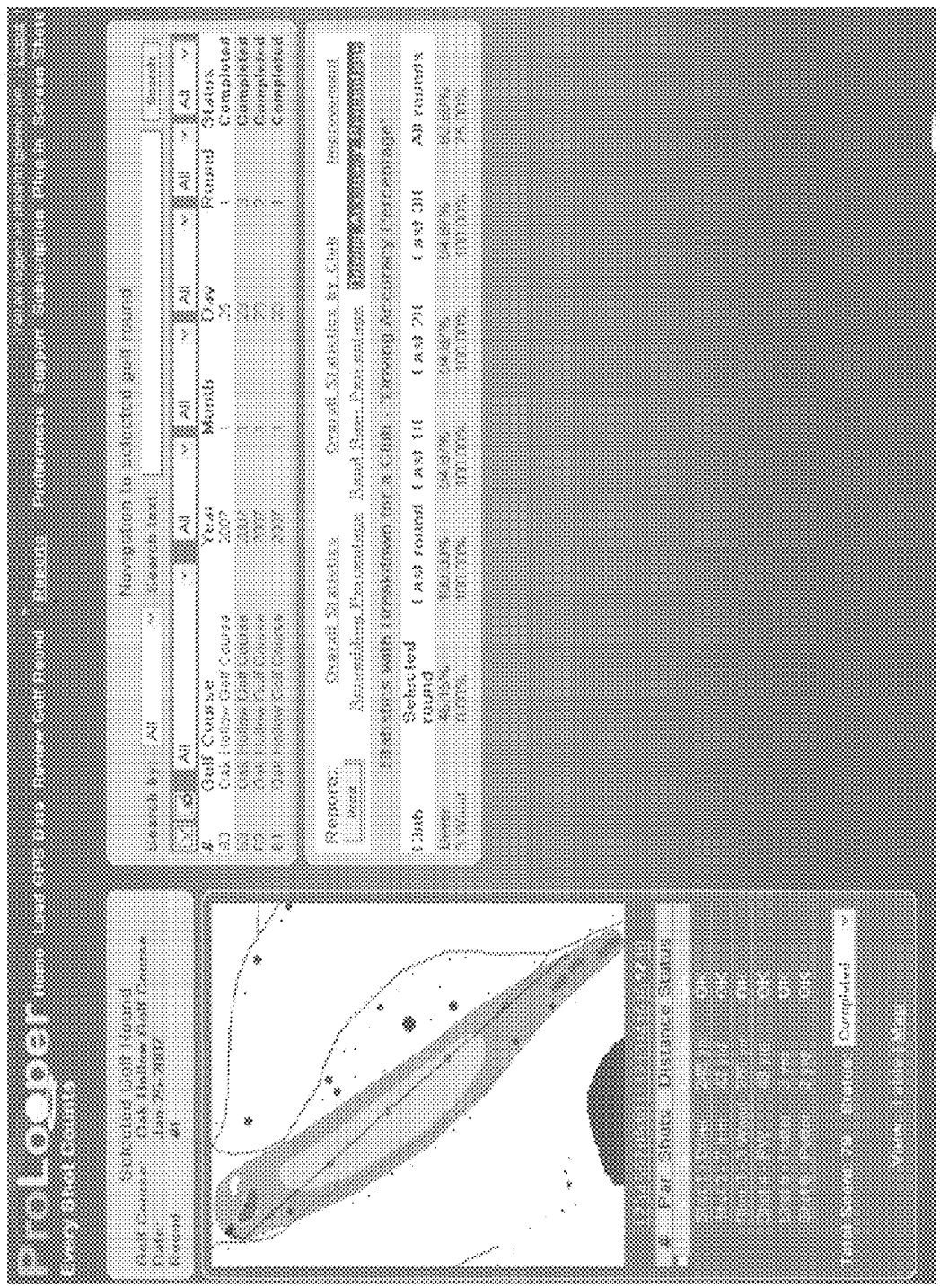

The next report illustrated in FIG. 22 shows a Scrambling Percentage report. This shows the user how often he/she makes par when he/she misses a green in regulation. Sand save reports show how often the user gets up and down out of a green-side sand bunker, as illustrated in FIG. 23. Driving Accuracy shows how often the user hits the fairway from the tee, as illustrated in the screen shot from the web-based user interface for FIG. 24.

Figure 25:
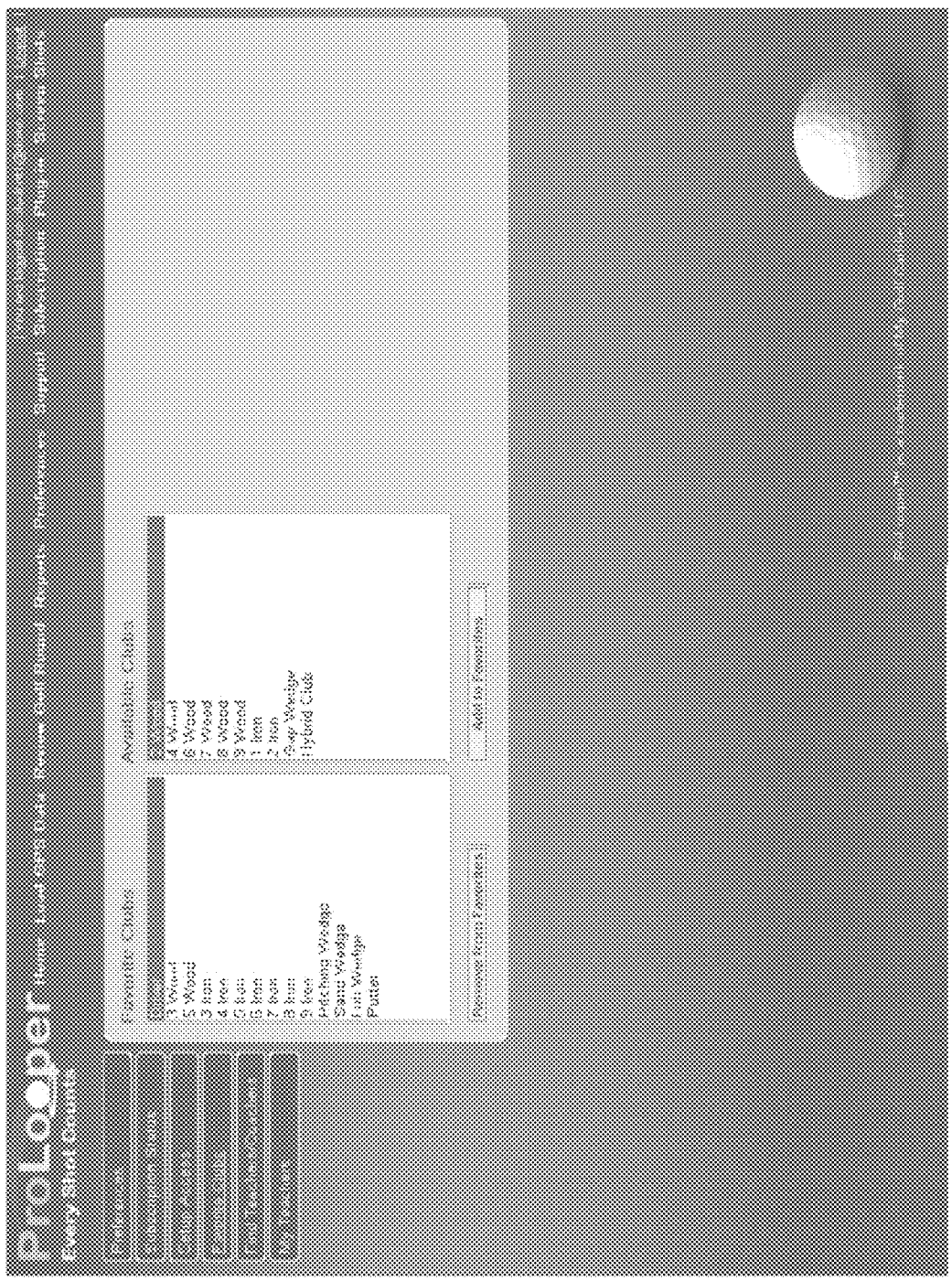

The system and methods of the present invention also provide for options that permit a golfer to set up favorite clubs, which prevents them from having to scroll through the entire list of clubs when reviewing shots on the user interface; this is illustrated in FIG. 25. To edit the properties of a particular shot, just click the shot. The user can add situational data such as lie, lay, slope, club, type of swing, weather information, etc.

Visualizations.

The present invention provides diagrammatic visualization of a target zone or area versus pinpoint target for a user providing inputs to the device, preferably the inputs being made during the course of play on a golf. The systems and methods of the present invention further provide for user access to statistical analytics and graphical user interfaces provided by software running on a remote server computer in communication with the user's computer via a network, preferably the web (WWW).

The present invention can provide detailed diagrammatic representations of golf performance analytics, such as scattergraph diagrams, that provide information including area and zone targets rather than merely pinpoint targets, and wherein the directionality of each shot is zeroed to facilitate identification of direction-based errors. Therefore, the present invention provides for situation-neutral golf metrics that are useful regardless of whether the application user is playing on a course or in a practice setting.

Preferably, the graphical visual representation(s) includes scattergraph diagrams and/or shot zone diagrams that identify errors and trends based upon the inputs for the at least one golf shot. Where the diagrams are viewable on the GUI or display, it is preferable that they be interactive. Also, the diagrams are viewable in a portable, printed pocket-sized version of the diagrams viewable on the GUI or display. In any format, the diagrams include shot accuracy based upon the at least one golf shot inputs for indicating performance for an individual golfer based upon a specific club and golf course situations, and past performance, along with statistical likelihood for present performance under similar conditions. The inputs include coordinates of a series of corresponding starting points and targets, recordation of actual shot locations from those starting points, and wherein the outputs include statistical analysis having text, tabular, diagrammatic, and/or image-based outputs that are converted from the inputs. The handheld device may either be a purpose-built golf GPS device or a mobile communication device, including but not limited to smart phones or mobile phones.

Regarding visualization of data, different visualization options of the shot data and related analytics are available, including tabular and map-type views, that are selectively reviewable by the user on the device, or on a remote computer connected to the server via the network, connected to the web. Additional shot-by-shot views and statistics are optionally reviewable by the user and/or a third party with permission for such review. In addition to the primary information, the user optionally enters secondary information, including but not limited to slope of the landscape between the ball and the inputted target, ball position on that landscape, wind direction, wind strength, precipitation, humidity, penalty strokes, altitude, player status (such as injury, sickness, etc.) and combinations thereof.

For scatter graph generation as shown in FIG. 1, the present invention systems and methods select shots made by a user using a specific golf club and for which flagstick is the target (in this case, a pinpoint target). Then the coordinates of the flagstick are projected for each shot in 0 point and find the distance from 0 point to: $Pn(x)$—distance in X-direction, $Pn(y)$—distance in Y-direction.

X-Direction Distance Calculation. The distance from target to shot in X-direction is calculated as follows: The reference point is taken as the coordinates of flagstick, to which the shot was targeted. The end point is $Pn(x)$, which is calculated as:

$Pn(x)$Longitude=Shot $n$ Longitude $Pn(x)$
Latitude=Target $n$ Latitude

Y-Direction Distance Calculation. For calculating distance from target to shot in Y-direction the similar method is used. The reference point is taken as the coordinates of flagstick, to which the shot was targeted. The end point is $Pn(y)$, which is calculated as:

$Pn(y)$Longitude=Target $n$ Longitude $Pn(y)$
Latitude=Shot $n$ Latitude

Positioning Shot by X, Y Coordinates. After the coordinates of $Pn(x)$, $Pn(y)$ have been found, we can calculate the distances from $Pn(x)$, $Pn(y)$ points to the Target. And this will be the distances of n-shot in X, Y directions. The distances are calculated with the help of GeoFrameworks library. Then it's needed to find the position of $Pn(x)$, $Pn(y)$ point relative to 0 point. At first we should determine the hemisphere of GPS coordinates. If hemisphere is South or West then we take those coordinates with negative sign.

If Longitude of $Pn(x)$ point is larger than Longitude of 0 point, it means that the point is located on the right (to the east).

If Latitude of $Pn(y)$ point is larger than Latitude of 0 point, it means that the point is located higher (to the north).

For instance, the following GPS Coordinates are received: End shot point latitude (2649.4087,N); End shot point longitude (08006.9080,W); Hole point latitude (2649.4087, S) Hole point longitude (08006.9100,W). To determine the position of the shot point relative to the hole by Y axe we should take shot point latitude with positive sign (because it's North hemisphere) and compare it with hole point latitude with negative sign (because it's South hemisphere). 2649.4087 is grater than (−2649.4087). So point is located higher (to the north). The same algorithm for determining the position by X axe. But in this case the West hemisphere is negative and the East is positive.

Updates to Support Direction of Play on Scatter Graph

Figure 2:
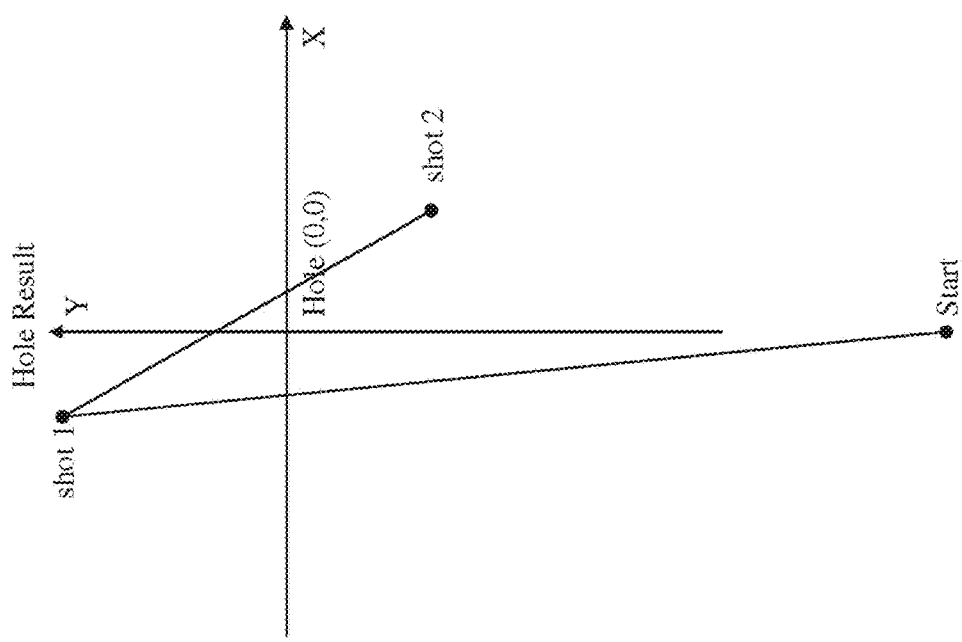
Figure 3:
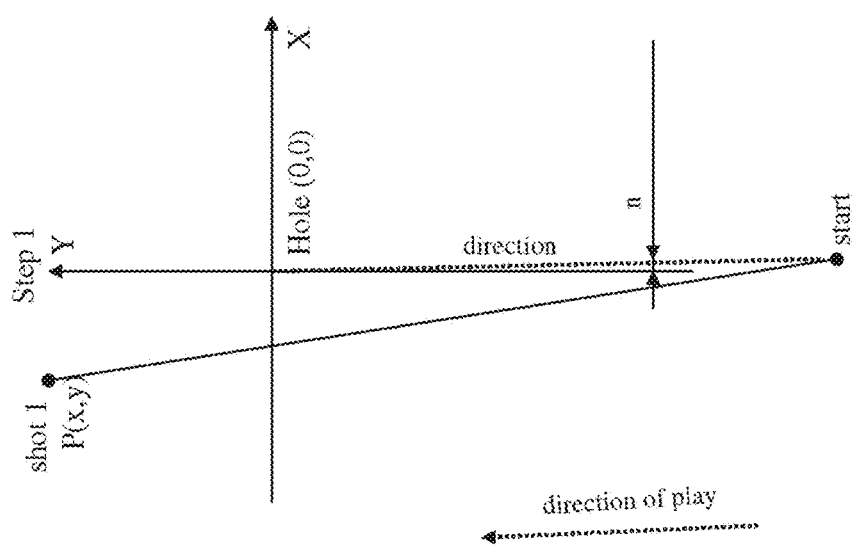
Figure 4:
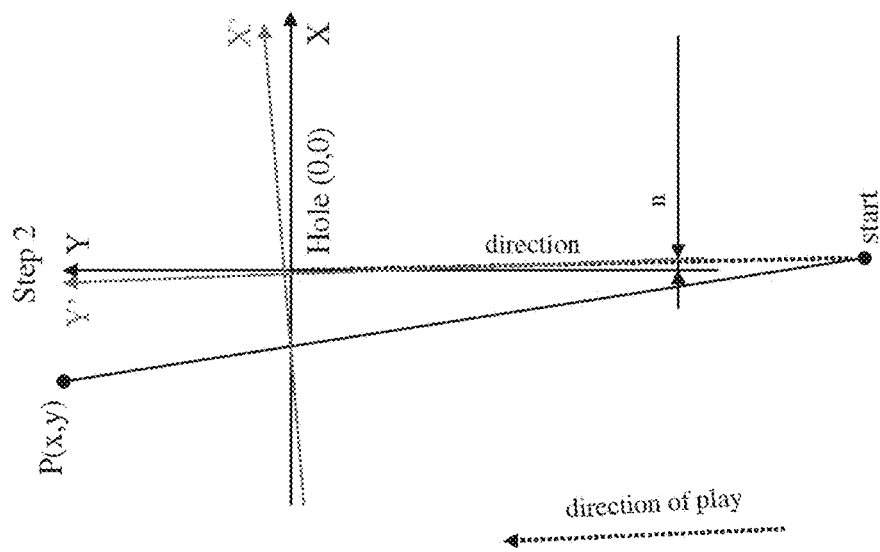
Figure 5:
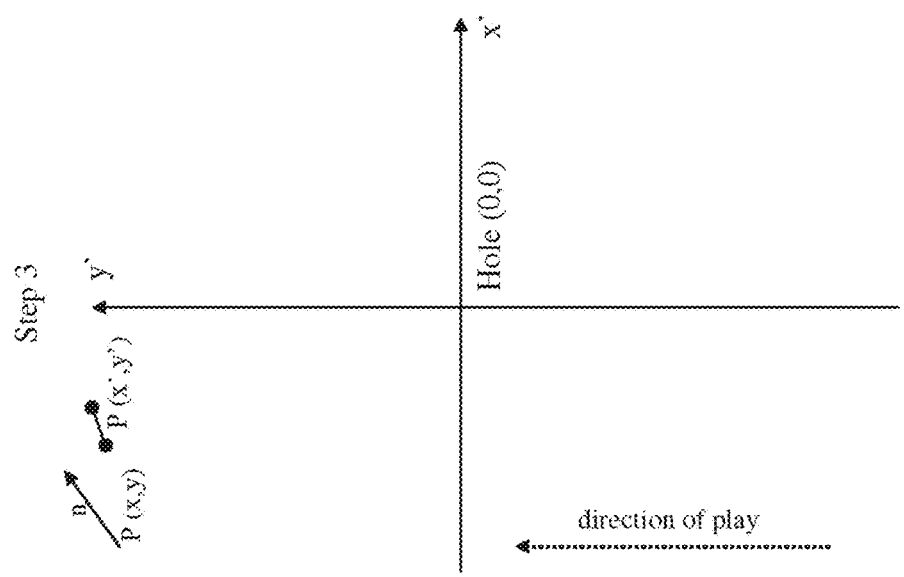
Figure 6:
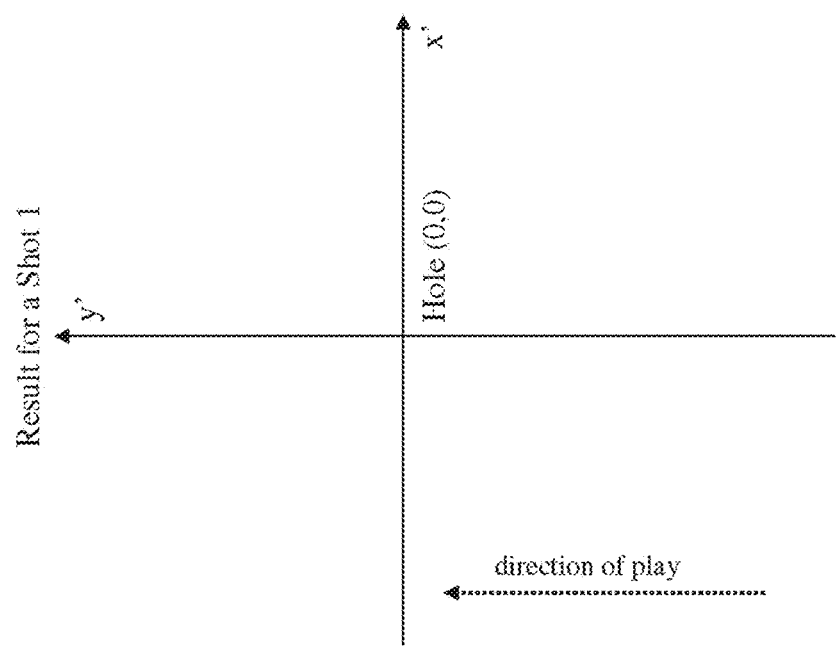
Figure 7:
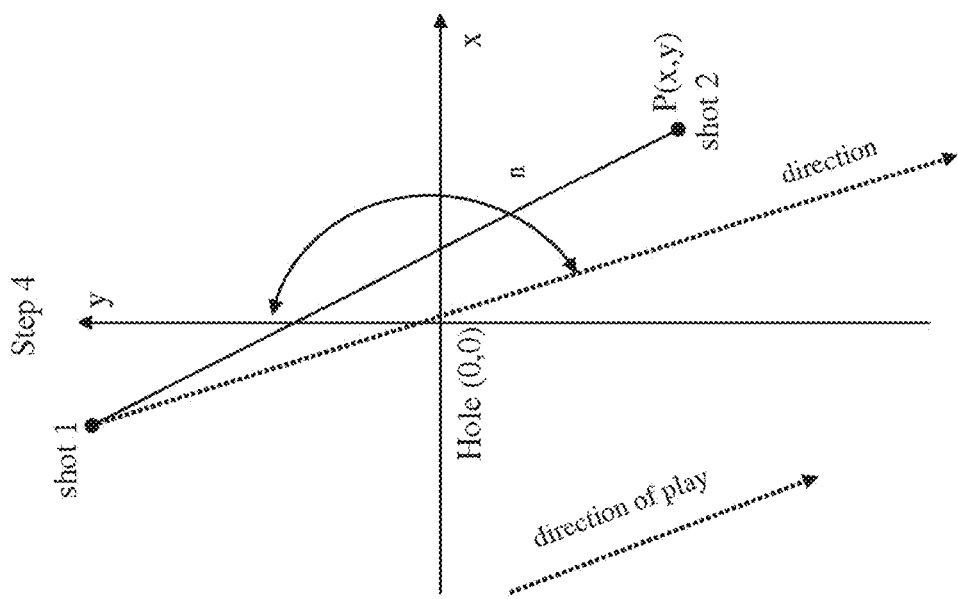
Figure 8:
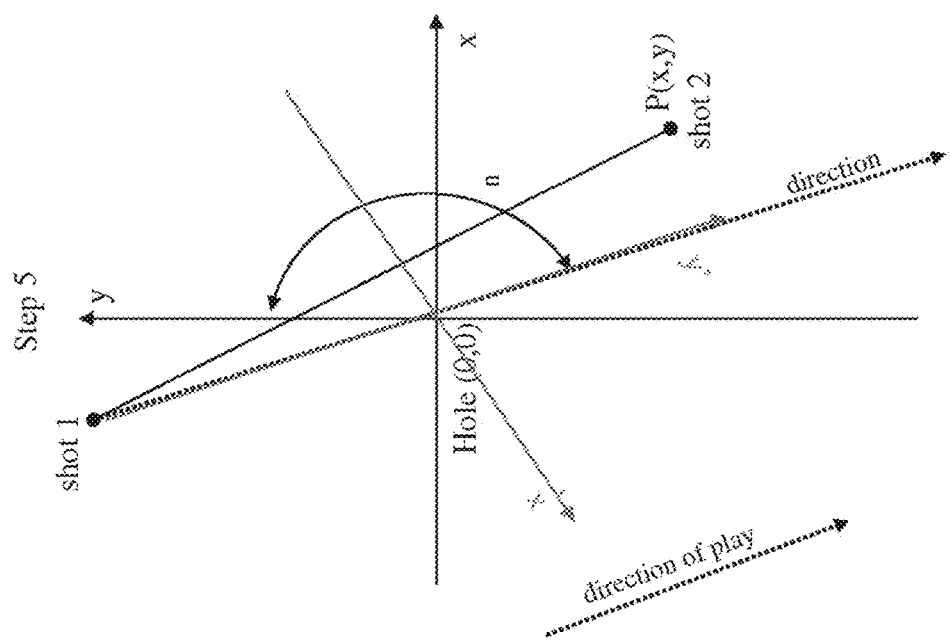
Figure 9:
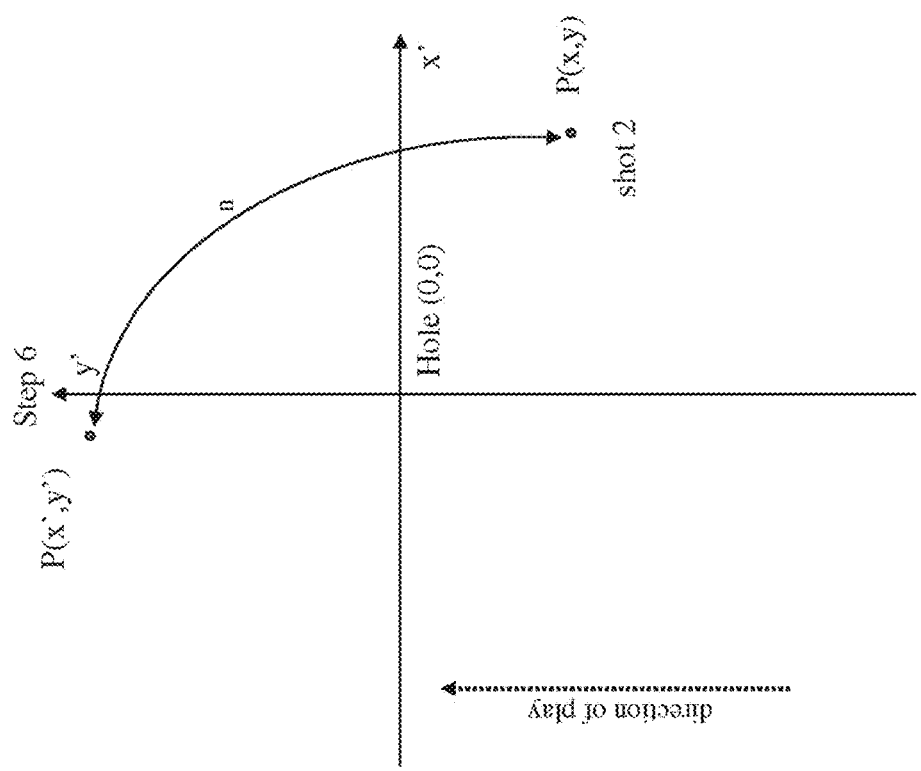
Figure 10:
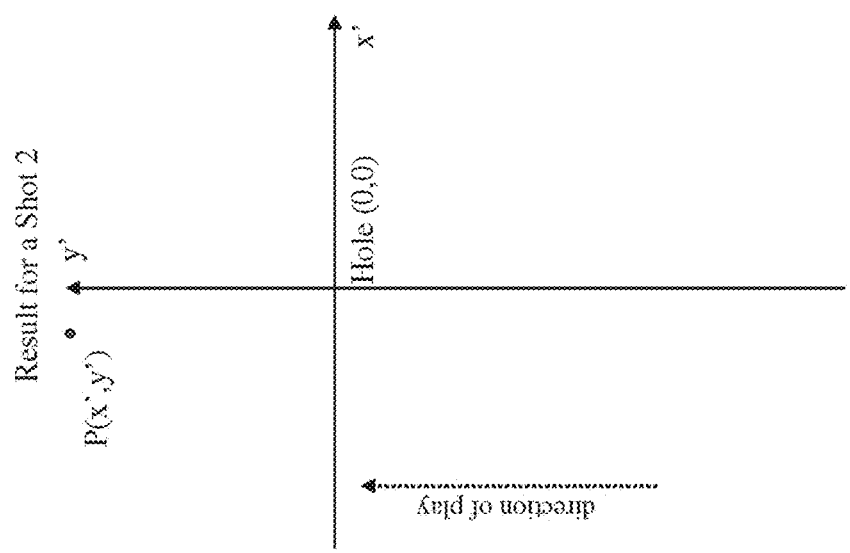
Figure 11:
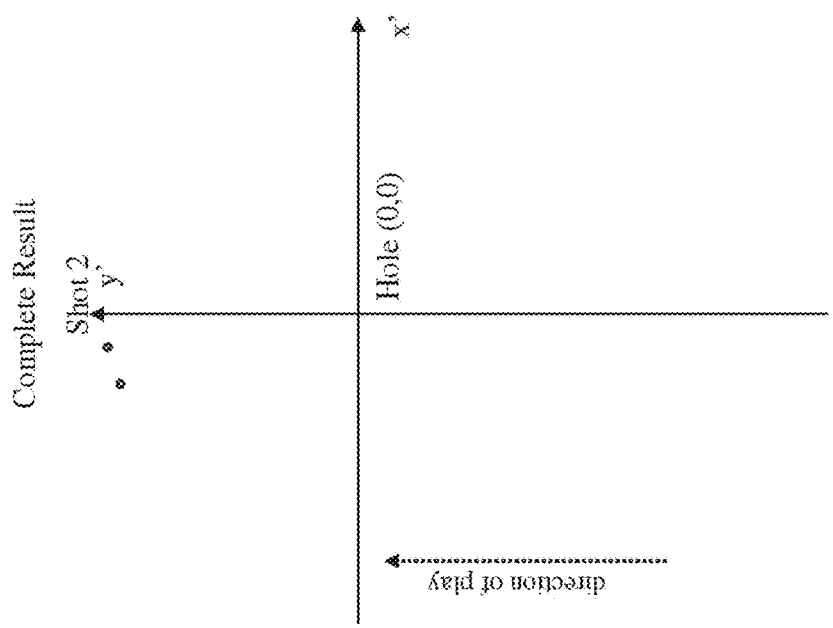
Figure 13:
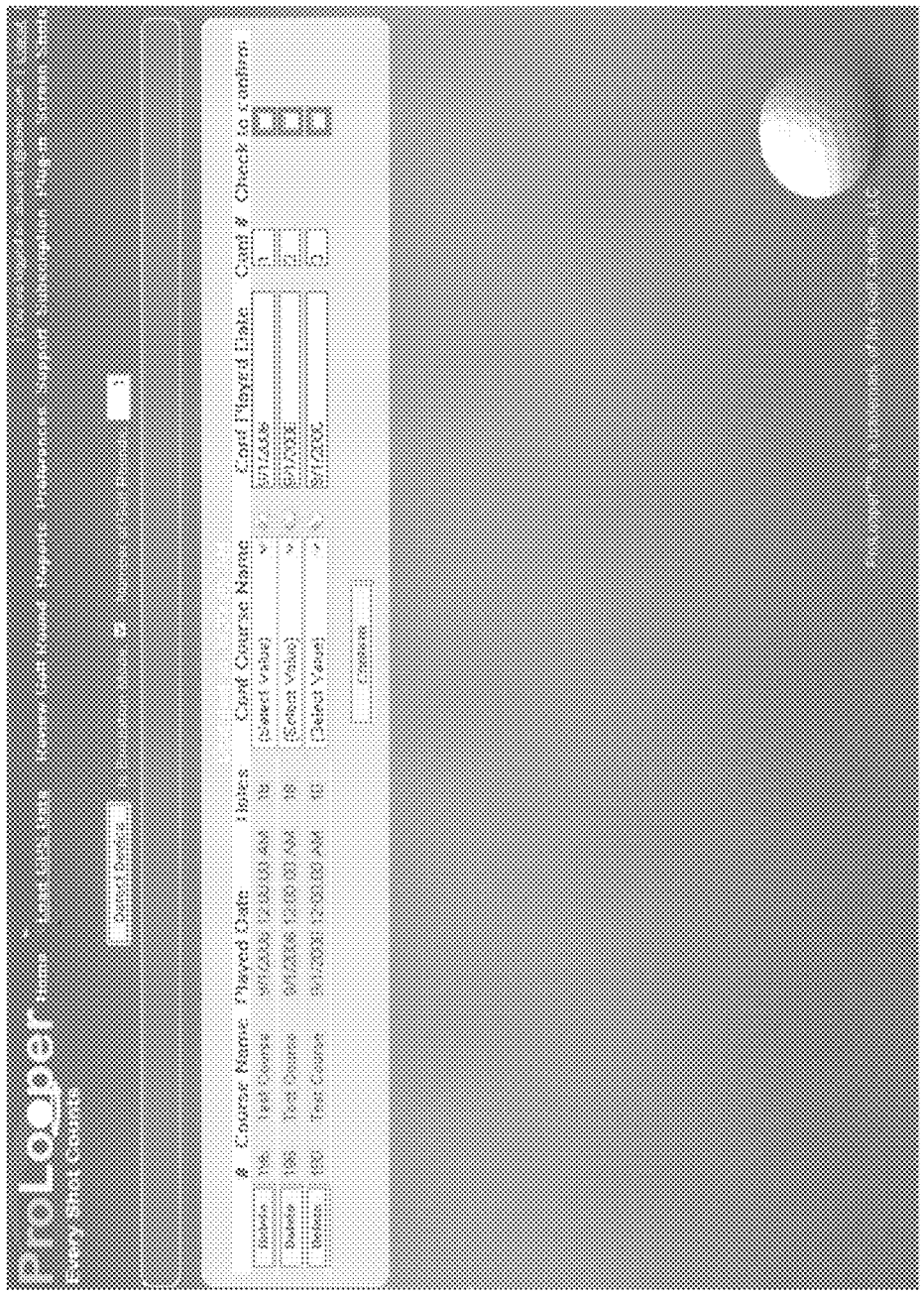
Figure 14:
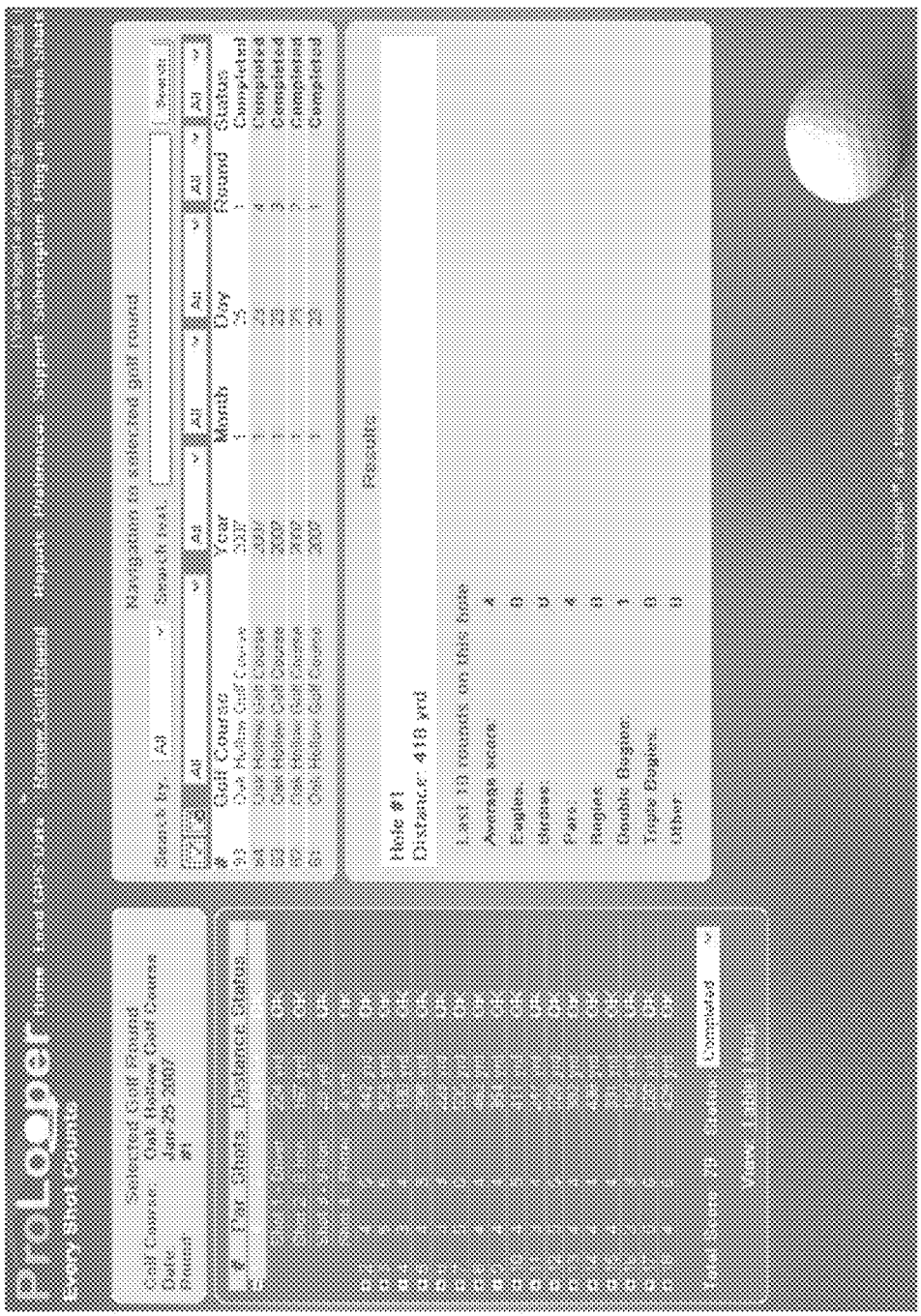

On FIG. 2, hole result is depicted. For graph calculation and diagram generation, the target for each shot is projected in point (0, 0). Then, by algorithm described in FIG. 2, the coordinates of point for each shot are calculated. FIG. 3 illustrates how the direction of the shot is found, as in Step 1. FIG. 4 shows the turning angle being found relative to the initial axes of reference, as in Step 2. FIG. 5 provides illustration of a Step 3, wherein the axes X', Y' and shot point are turned through angle n.degree., resulting in a graph illustrated in FIG. 6, showing a result for a shot 1 or a first shot. A similar method is used for generating the point of a second shot or subsequent shot, as shown in Step 4, Step 5, Step 6, Results for a shot 2 in FIGS. 7, 8, and 9, respectively, with the FIG. 10 showing a result for shot 2. Then, the graphs for each separate shot are merged together resulting in the complete Hole Result, illustrated in FIG. 11.

Printable Cards.

In addition, the present invention provides a portable and preferably pocket-sized printed version of shot performance and/or statistical likelihood of present or future performance based upon past performance for any given golf club, golf course conditions, etc. Preferably, the shot zone diagrams provide a visual representation of statistical likelihood for any given shot based upon past performance. The shot zones preferably include a range of probability, such as 90%, 70%, and 50% likelihood. The shot zones may be developed based upon the actual past performance and/or may be based upon actual past performance plus a factor for variation and projection of likelihood of shot accuracy for the instant shot, depending upon conditions, etc. The past performance data is preferably selected from a predetermined range of time to include more than one past performance for an individual golfer. It may be selected for play only on a given course (such as the same course being played at that time), or may be selected from all past play on any course. The data is updatable and can be stored on the device and printed from an electronic dataset that is preferably generated as set forth in the description infra. In any case, the shot zones are the best manner for the golfer to estimate how and where he should take the shot, with which club, for the conditions present at that time. Thus, the pocket-sized, printed version of these diagrams provides a personalized shot book for an individual golfer that can be used during play on any course, even during tournament play.

It will be appreciated by one of ordinary skill that the current rules of golf do not allow for electronic devices to be used on the golf course during play. Therefore, the preferred embodiments provide for printed versions. However, it is included within the scope of the present invention that the shot zone diagrams may be viewable and provided on electronic, handheld devices such as purpose-built GPS devices, mobile phones with graphic user interface screens, PDAs, and the like. These are currently available but are also currently not allowed during tournament play. Thus the "shot book" is intended to include electronic views not in printed, book or booklet form, but in screen shot or GUI viewable form.

The shot zone of the present invention set forth hereinabove may be supplemented with scattergraph diagrams as set forth herein. The system and methods of a preferred embodiment for determining the past performance of an individual golfer are set forth herein. It will be understood and appreciated by one of ordinary skill in the art that other methods, including manual recordation of past performance, may be used to generate the data from which the shot zone and the corresponding diagrams for a shot book are developed. The present best mode, however, provides that these are generated automatically, based upon data input during the golf round(s) using a hand-held GPS device and a software for inputting and analyzing the golf game data.

Coaching.

Additionally, the golfer has review options provided on a graphical user interface on a GUI or display for reviewing, editing, modifying, and adding data to the uploaded shot data. In another embodiment, a method for providing statistical analytics of golf performance includes the steps of providing a GPS-operable device for a user to input golf shot data during play on a course; uploading the golf shot data including GPS data to a computer having software for providing analysis of the data; and providing outputs including analytics of the data, wherein the outputs are viewable by the user via a GUI or display via text, tabular, graphic, and image-based outputs that include trends information for the golfer, all based upon actual golf play on course situations, wherein the golfer inputs shot data during play, without interrupting the flow of the game, and uploads the shot data for analytics and review online. In such an embodiment the analytics preferably include text, tabular, graphic, and image-based outputs that include trends information based upon the shot data input by the user, wherein the shot data is based upon actual golf play on course situations, and the golfer inputs shot data during play.

Figure 26:
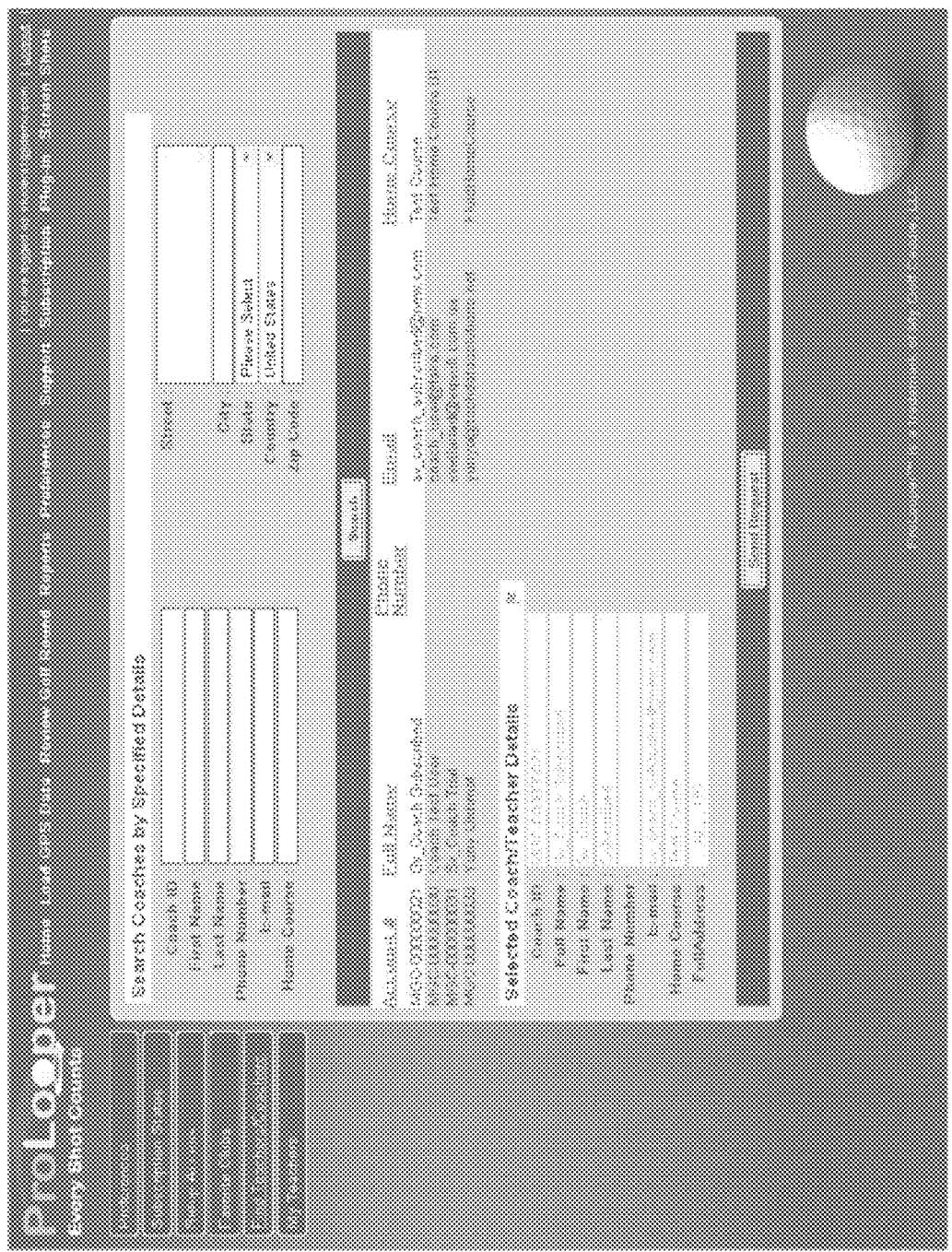

The system and methods of the present invention also provide functionality that permits a user to allow or provide access to another user such as their coach or a PGA professional. In one embodiment of the present invention, this is done by a user making a click-select of the "Find Teachers/Coaches" link in the Preferences section (coaches and PGA Pros may check a box that identifies them as a coach/teacher when they sign up). The user finds a coach/teacher, and clicks the "Send Request" button or option, as illustrated in FIG. 26.

Figure 27:
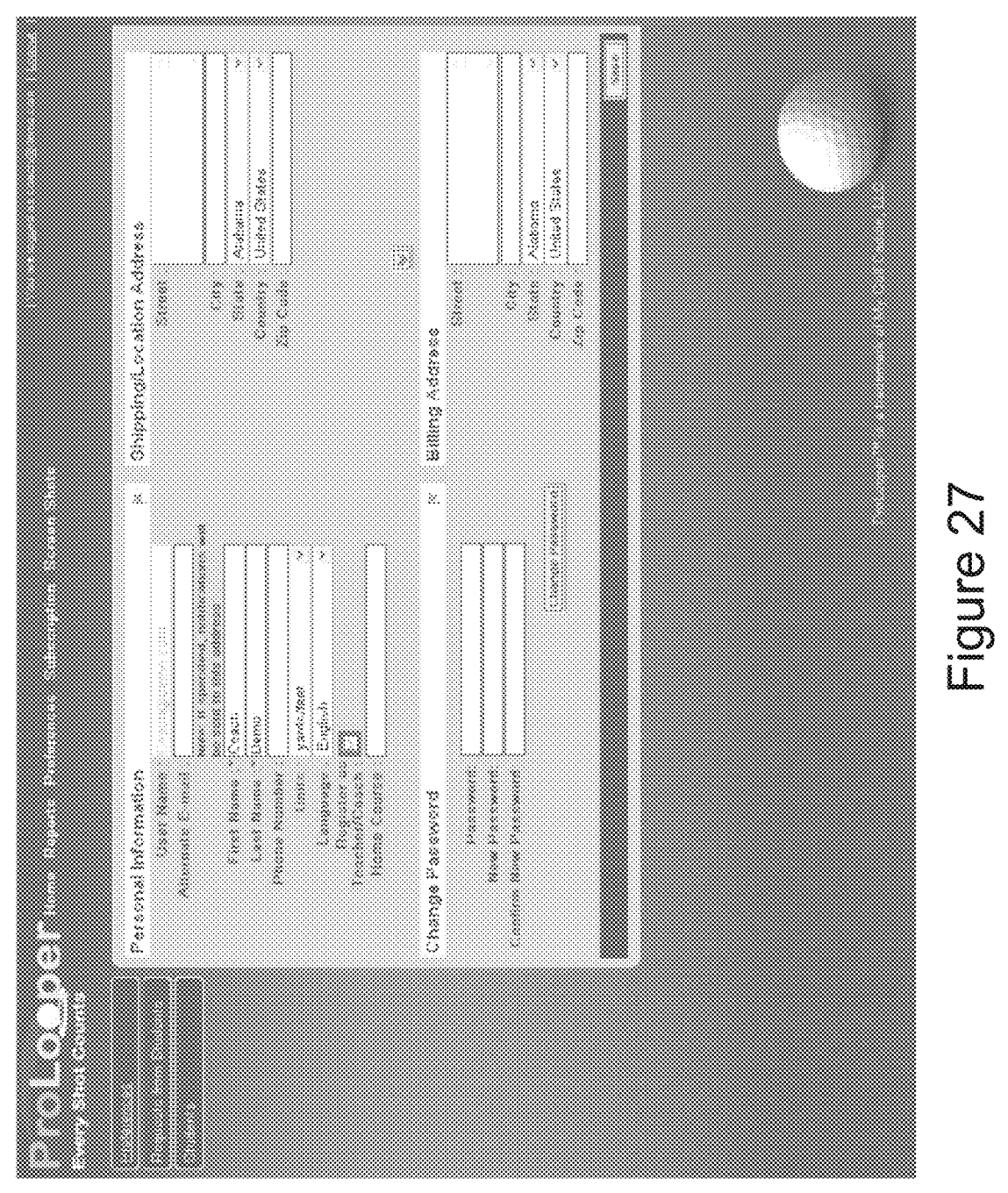
Figure 28:
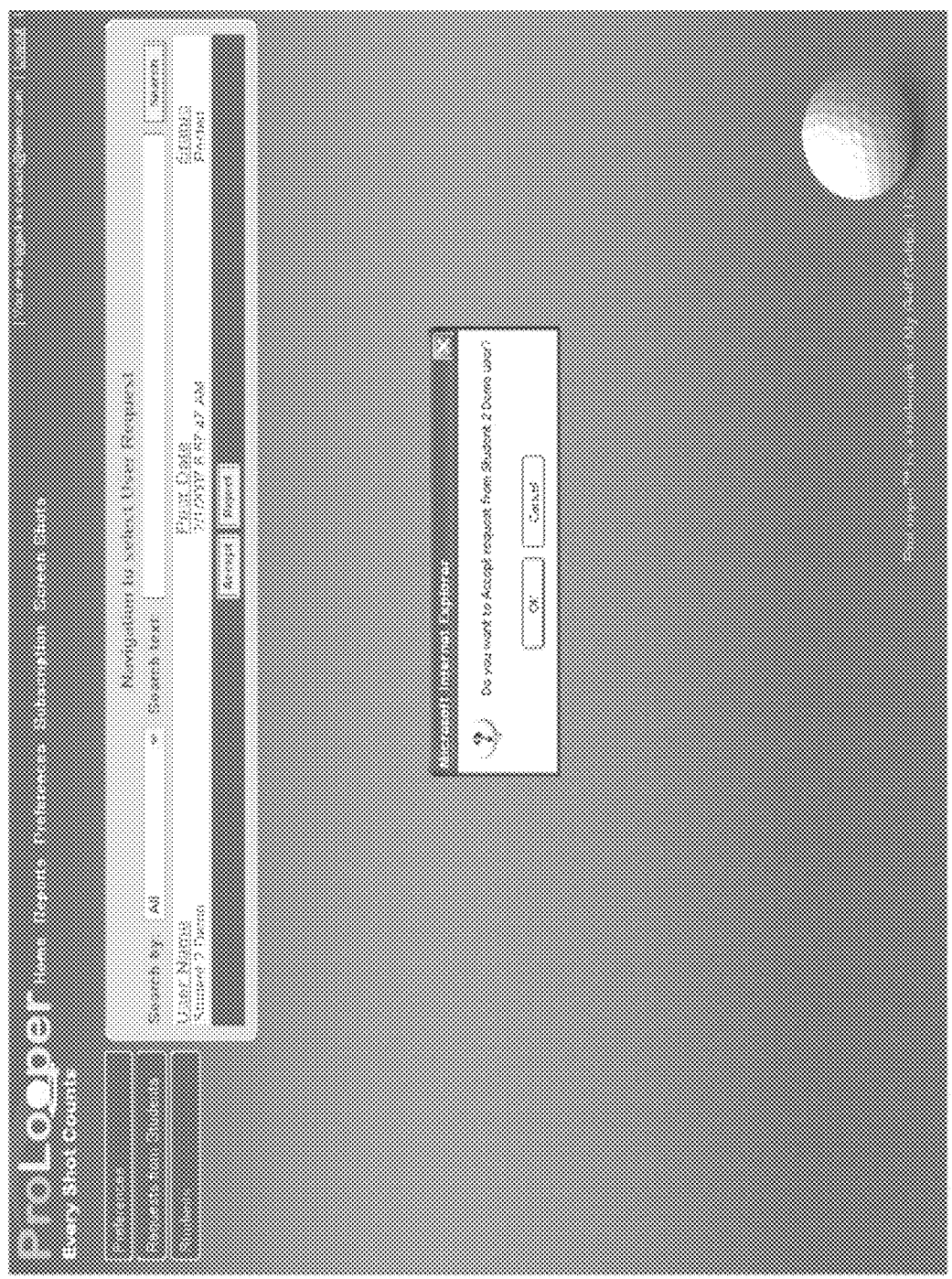
Figure 29:
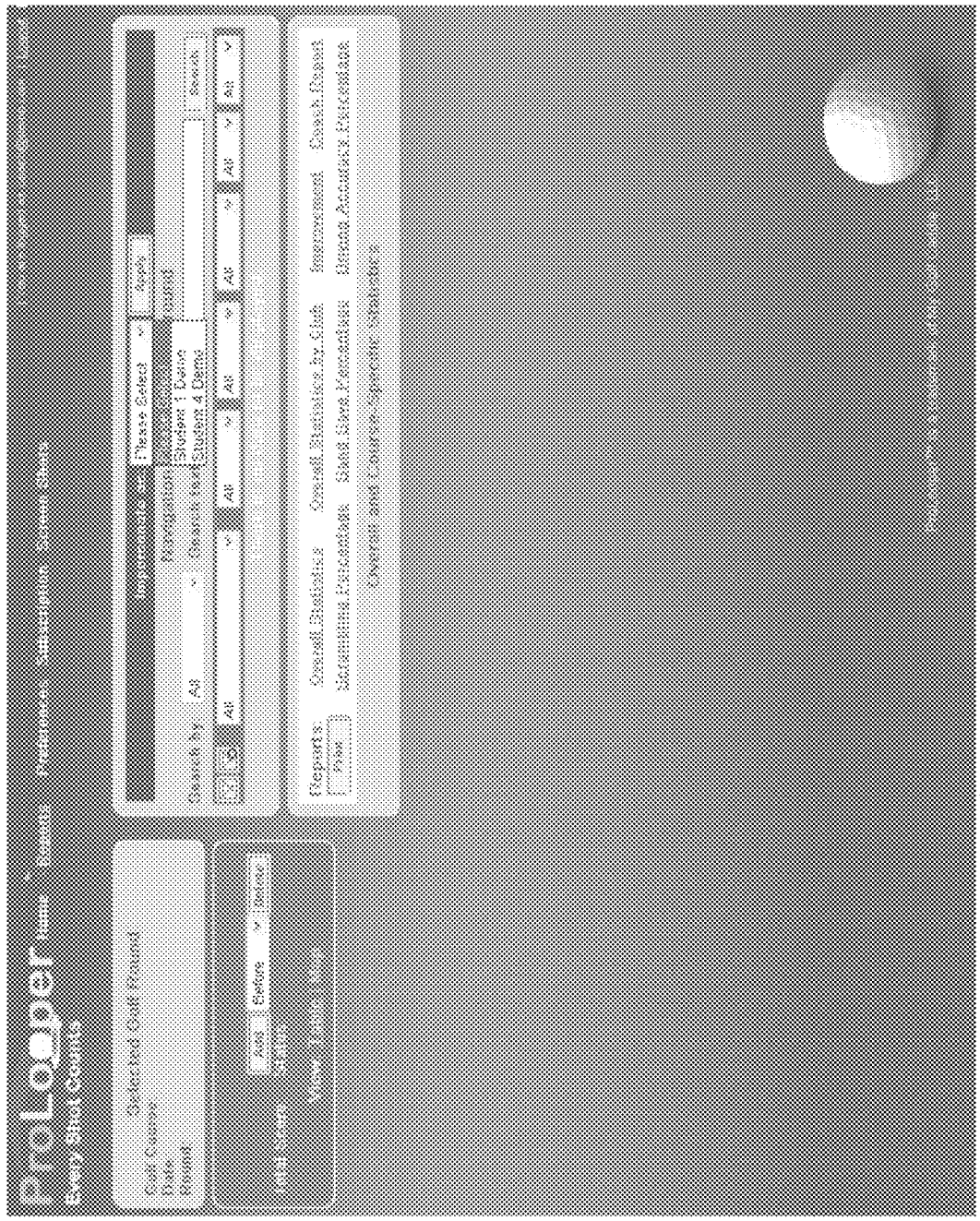

FIG. 27 illustrates a graphic user interface that provides options for coaches and teachers to sign up to receive notices and review rounds actually made by their students who have extended access to the data to them. After a student sends a request to a coach/teacher, the coach/teacher is provided the option to log in for viewing an interface as illustrated by FIG. 28. Once accepted, preferably the coach/teacher can then view, but cannot make changes to, all the reports that the golfer or user also reviews. The coach/teacher click-selects or indicates the desired golfer from a listing such as the "Impersonate as" drop-down menu, and all of that golfer's reports are available, as shown in the FIG. 29.

Figure 30:
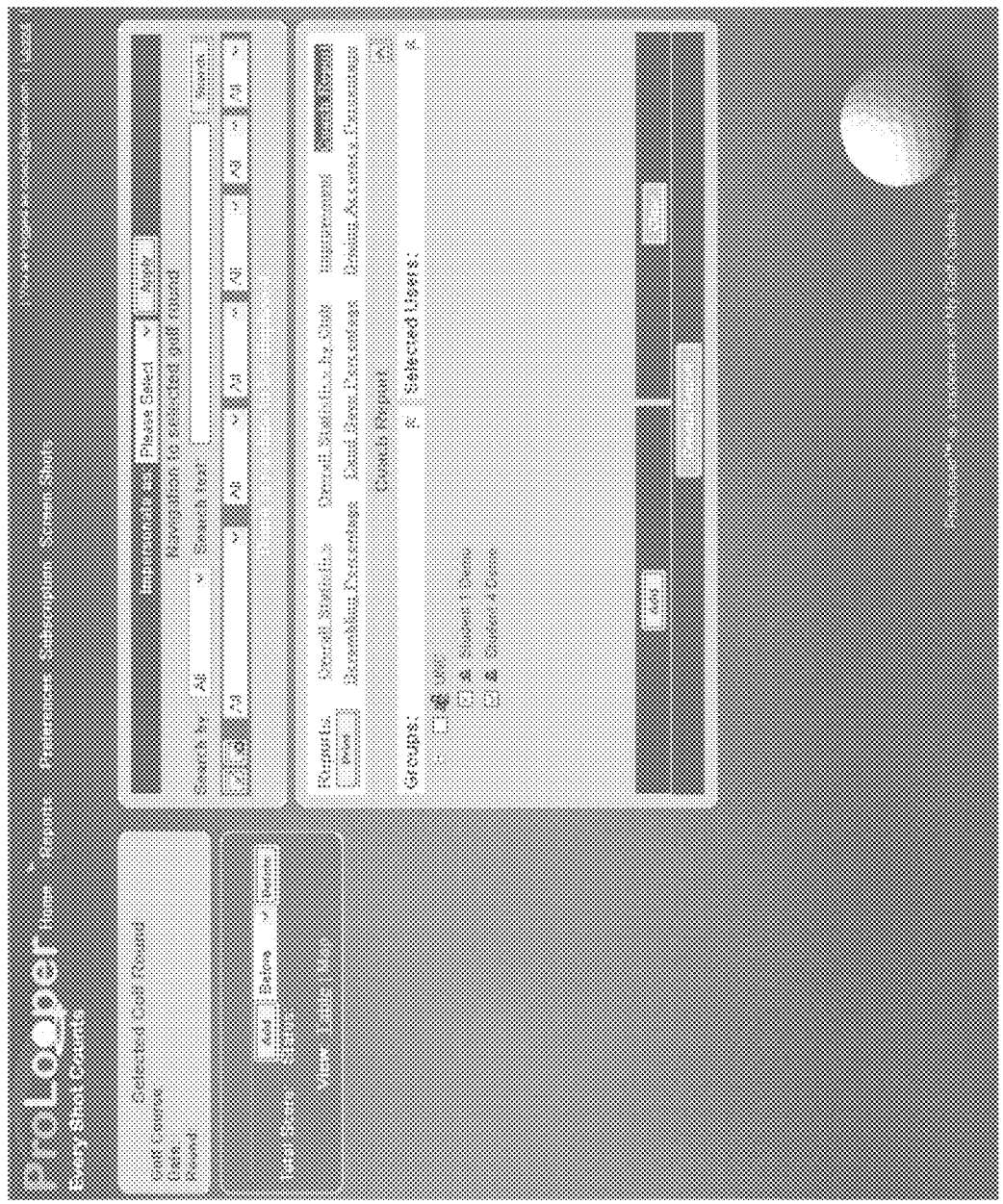

As illustrated in FIG. 30, the systems and methods of the present invention provide coach/teacher with the option to create a report that compares multiple golfers or users, preferably side by side. By click-selecting another option, such as "Coach Report", they see a list of all golfers they have access to. They then select which of these golfers to compare, and click-select "Add." Preferably a multiplicity of golfers or users' data is available for review and comparison by the third party coach/teacher.

Figure 31:
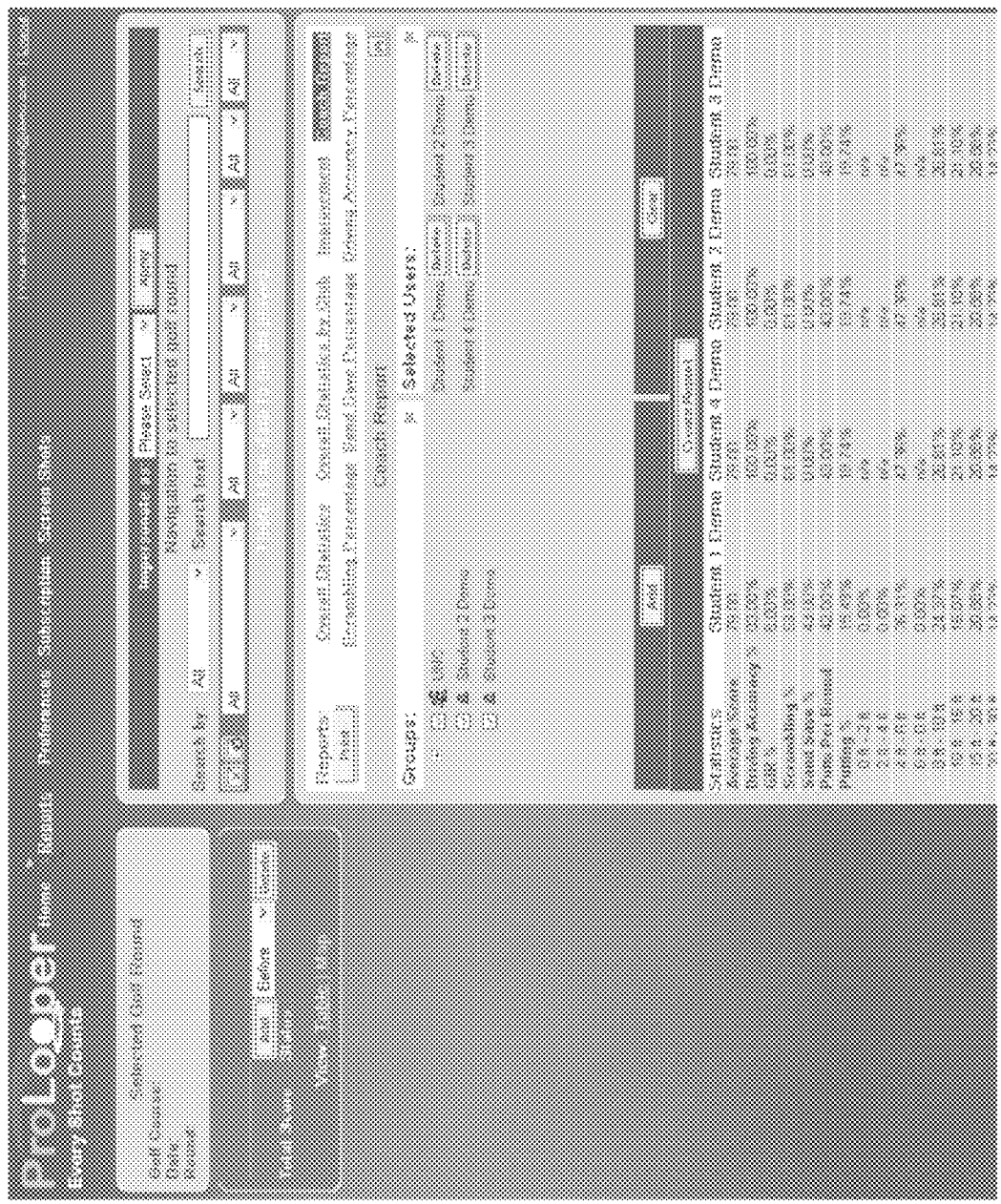

As illustrated by the screen shot in FIG. 31, the user then click-selects a "Create Report" button to view the report, showing those selected users or golfers in a comparative manner, preferably with data in tabular format side by side, but optionally in an overlay graphic of shots or other visualization that facilitates comparison or analysis.

The present invention provides visual diagrammatic views including scattergraph diagrams that provide for the directionality of any shot to be uniformly and consistently oriented to provide a zeroed-out orientation for each shot thereby assisting the user/golfer with identification and understanding of errors and trends related to shot misdirection and the corresponding causes related thereto, so that adjustments to form, strategy, and ultimately performance can be made by the user and to which the coach user has access through a web-based account for reviewing the data and providing feedback to the user regarding corrective action or recommendations for improvements.

The system further provides for a unique login for each user, including both application users (students) and coaches/instructors/teachers to access the remote server computer for making data and informational inputs, and for modifying and adding information, including secondary information that includes more detail about play conditions, user status, etc. and coaching-specific information such as corrective actions or recommendations for improvement.

Another aspect of the present invention is to provide methods for statistical analysis of golf performance of a user including the steps of the user inputting information and corresponding coordinates for a series of shots including a start point and a target area, as well as actual shot location throughout a course of play; the user uploading that information and data to a remote server computer, where software is operable to perform statistical analysis and provide outputs to the user relating to trends in the user's performance over a predetermined period; wherein the scattergraph diagrams include information relating to the directionality of any shot to be uniformly and consistently oriented to provide a zeroed-out orientation for each shot, thereby assisting the user/golfer with identification and understanding of errors and trends related to shot misdirection and the corresponding causes related thereto, so that adjustments to form, strategy, and ultimately performance can be made by the user and for an authorized coach user accessing user information and data, including analytics thereon and providing tracking of coaching recommendations and successful implementation thereof.

The present invention provides a system for providing statistical analysis for golf performance of a user including a portable input device, preferably a handheld device with GPS-functionality, operable for capturing shot data during the golf play of a golfer, the device being further operable to transmit the shot data and related GPS data to a computer for reviewing the shot data and analysis of the shot data through a graphical user interface viewable on a GUI or display; the computer further including software operable for providing statistical analysis of the shot data; wherein the user provides inputs and coordinates of a series of corresponding starting points and target areas, and recordation of actual shot locations from those starting points during the golf play via the device; and wherein the statistical analysis includes outputs relating to the golfer's golf performance over a predetermined period, and wherein the outputs include scattergraph diagrams having information relating to the directionality of any shot to be uniformly and consistently oriented to provide a zeroed-out orientation for each shot, thereby assisting the user/golfer with identification and understanding of errors and trends related to shot misdirection and the corresponding causes related thereto, so that adjustments to form, strategy, and ultimately performance can be made by the user; the user uploading the shot data to a remote server computer; software operable on the computer performs statistical analysis of the shot data associated with the golfer; and the software providing analytics outputs to the user via a GUI or display having a graphical user interface, including trends in the golfer's performance over a predetermined period.

Figure 32:
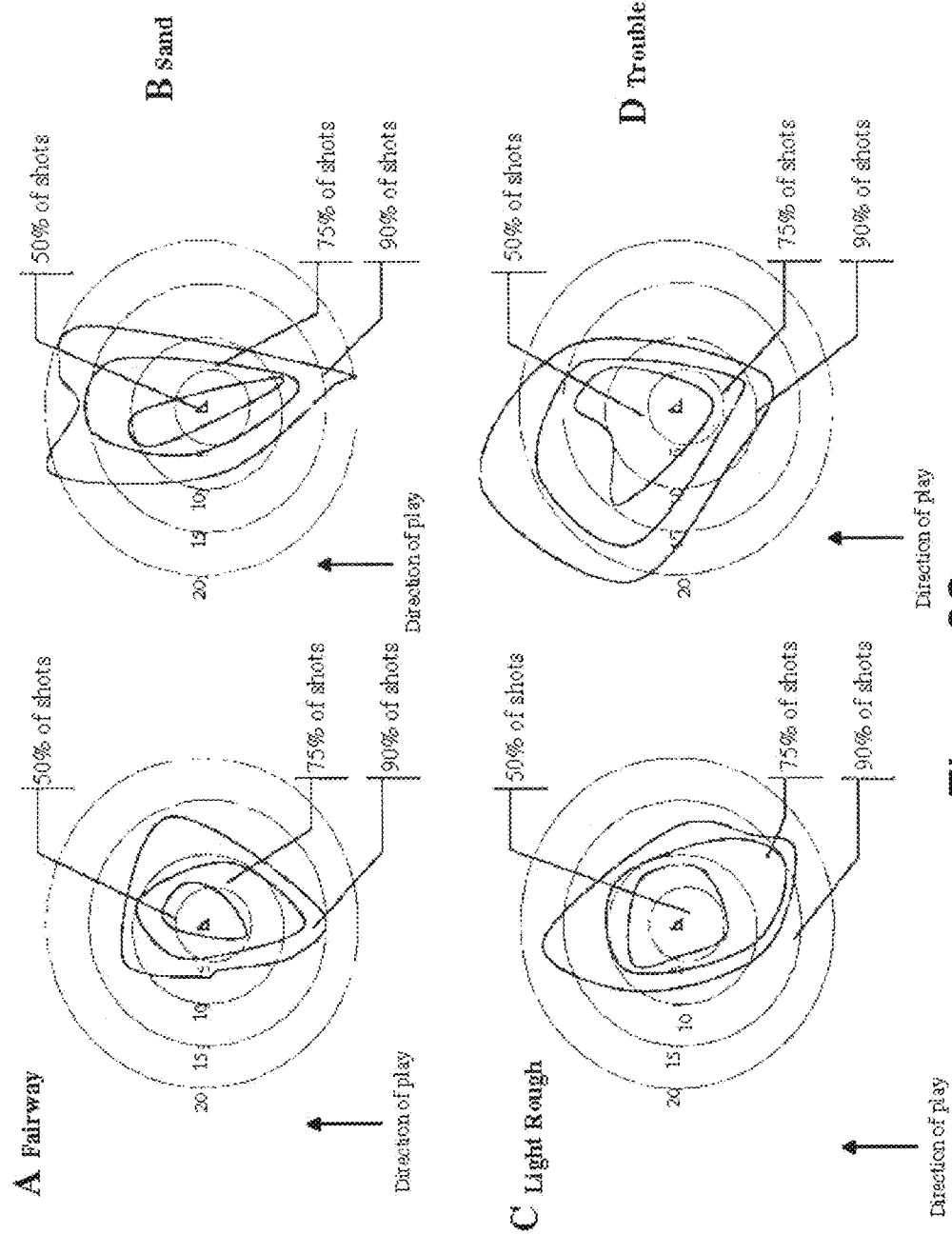
FIGS. 32 and 33 show shot zone diagrams for given golf club and select golf course locations and/or conditions.
Figure 33:
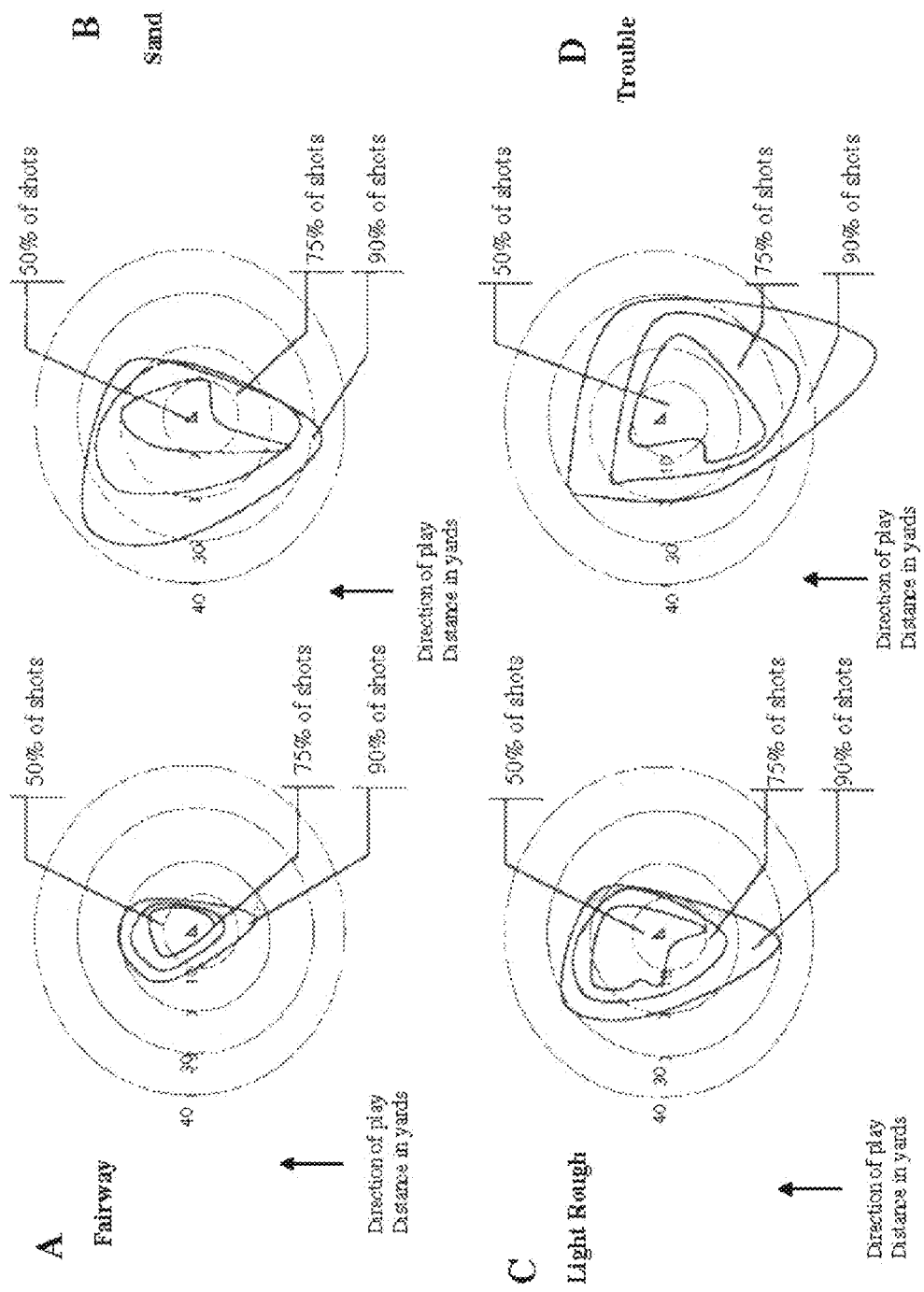

FIGS. 32 and 33 show shot zone diagrams for a given golf club and select golf course locations and/or conditions. FIGS. 32A-D show variations for a pitching wedge. Direction of play is indicated by an arrow at the lower left hand corner of the diagram for each condition. Golf course locations and/or conditions are illustrated here for fairway, sand, light rough, and trouble. Other locations and/or conditions may be provided in substitute or addition to any of these. FIGS. 33A-D show variations for a 6 iron. Note also that for each of the illustrated golf clubs, the dates for which the statistical likelihood are illustrated are listed below each golf club. This may be developed over a shorter or longer period of time, and the time frame is provided for illustration only. Depending upon the amount of golf played by an individual golfer, the statistical significance and likelihood algorithms may be adjusted and/or may simply have fewer or greater data points from which to make the projections.

Figure 34:
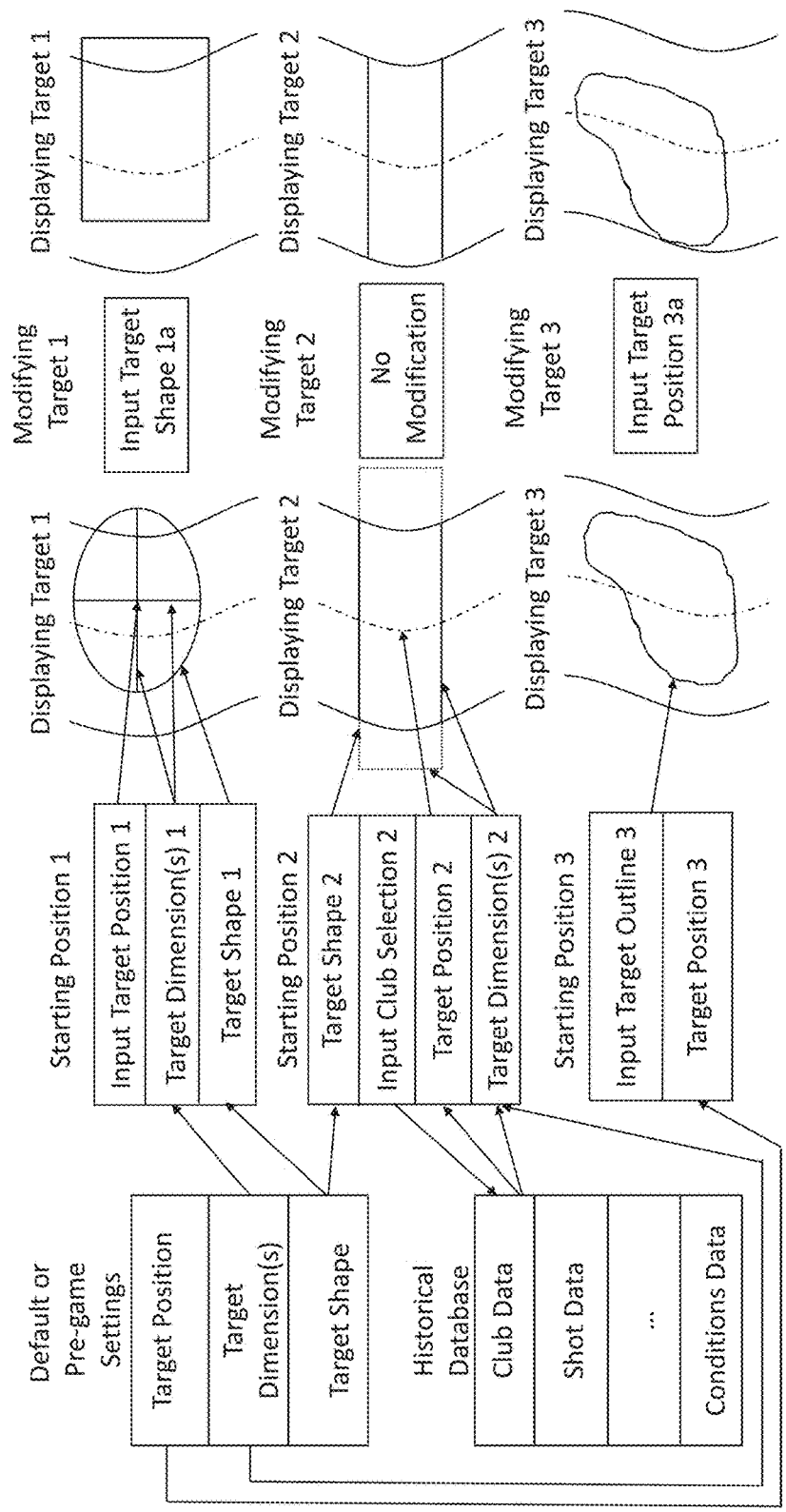
FIG. 34 is a flow diagram illustrating several embodiments of a device receiving a target for statistical analysis.

FIG. 34 is a flow diagram illustrating several embodiments of a device receiving a target for statistical analysis. In one embodiment, from starting position 1, the device receives a target position input and displays a target by using the default target dimensions and target shape previously inputted. In this embodiment, an oval was inputted as the default target shape, with a width dimension slightly larger than the height dimension (e.g., 25 yards by 20 yards), and with the center of the oval equal to the inputted target position. Upon viewing the displayed target the user decides to modify the shape by selecting a new target shape—a rectangle. Therefore, the device modifies the display such that the center of the shape remains equal to the inputted target position, the dimensions of the shape remain equal to the default target dimensions, and the shape outline is changed from an oval to a rectangle. In alternative embodiments, the user may input additional modification following the second target display.

FIG. 34 illustrates another embodiment of the invention in starting position 2. The devices receives an inputted club selection, retrieves data from the historical database and pre-game settings and displays the resultant target. In this example, the default target shape is a rectangle including the setting to be confined to a fairway or green. The target position is calculated using the club data, such that the average club shot for the account may be used to calculate the target position, centered in the fairway. The target dimensions are calculated using the club data, such that the default target dimension setting is used to determine what percentage the length and width of the rectangle is to be. Although not explicitly illustrated, in another embodiment the target position may be calculated using shot data and default or pre-game settings such that the target position is equal the average club shot for a group of accounts less 5% of the average club shot yardage. In the embodiment of starting position 2, the calculated target extends beyond the fairway (shown by the dotted lines) so the device modifies the target to be confined to the fairway (shown by the solid lines).

FIG. 34 additionally illustrates an embodiment for starting position 3. The device receives an inputted target outline and receives a target position from the default settings. Alternatively, the target position could be calculated based on an inputted club selection or combination of an inputted club selection and default position settings. The device then displays the inputted target area centered on the default target position. The center of a custom inputted target area can be calculated in a number of ways know to those skilled in performing such calculations, but one method would be to use the center of a largest inner circle to fit within the shape and an alternative method would calculate an average width and height to use as the center. Referring back to the illustration, the user may input a new target position by simply dragging and dropping the target to a new position or using another input mechanism.

Figure 35:
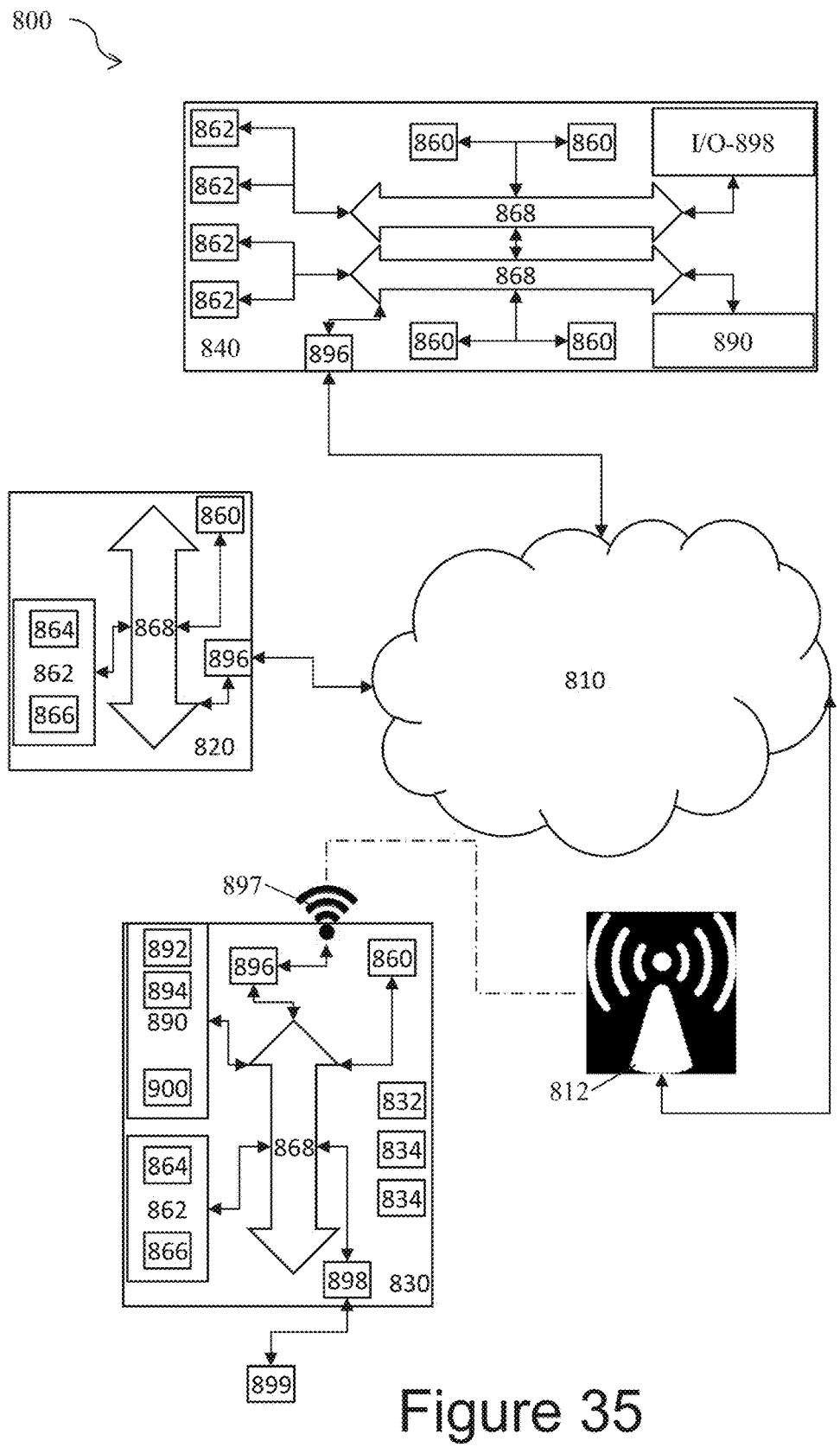
FIG. 35 is a schematic diagram illustrating a computer system for the present invention.

FIG. 35 is a schematic diagram of an embodiment of the invention illustrating a computer system, generally described as 800, having a network 810 and a plurality of computing devices 820, 830, 840. In one embodiment of the invention, the computer system 800 includes a cloud-based network 810 for distributed communication via the network's wireless communication antenna 812 and processing by a plurality of mobile computing devices 830, 840. In another embodiment of the invention, the computer system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital devices 820 and mobile devices 830, 840 such as a server, blade server, mainframe, mobile phone, a personal digital assistant (PDA), a smart phone, a desktop computer, a netbook computer, a tablet computer, a workstation, a laptop, GPS-enabled device and other similar computing devices. The components shown here, their connections and relationships, and their functions, are meant to be exemplary only, and are not meant to limit implementations of the invention described and/or claimed in this document.

In one embodiment, the mobile device 830 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. Further, the mobile device 830 may include a graphic user interface or display 832 and various input mechanisms 834. The input/output controller 898 may receive and process input from, or provide output to, a number of other devices 899, including, but not limited to, alphanumeric input devices, mice, electronic styluses, display units, docking stations, charging stations, touch screens, signal generation devices (e.g., speakers) or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown in FIG. 35, a computing device 840 may use multiple processors 860 and/or multiple buses 868, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to the bus 868. Computing devices may communicate communication media through wired networks, direct-wired connections or wirelessly such as acoustic, RF or infrared through a wireless communication antenna 897 in communication with the network's wireless communication antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications or other data embodying any one or more of the methodologies or functions described herein. The computer readable medium may include the memory 862, the processor 860, and/or the storage device 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory or other solid state memory technology, disks or discs (e.g., digital versatile disks (DVD), HD-DVD, BLU-RAY, compact disc (CD), CD-ROM, floppy disc) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 may not include all of the components shown in FIG. 35, may include other components that are not explicitly shown in FIG. 35, or may utilize an architecture completely different than that shown in FIG. 35. The various illustrative logical blocks, modules, elements, circuits, and algorithms described in connection with the embodiments disclosed herein may be implemented as electronic hardware, computer software or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

For example, the computer system may include a remote server computer (RSC), wherein the shot data is uploaded from a mobile device to the RSC through the network and the course data is downloaded from the RSC to the device through the network. The RSC may store and analyze the data for user access and review, the data being accessible via the Internet or worldwide web network. Alternatively, RSC data can be downloaded to and stored on the device for use when the Internet is not available. The user may be provided a unique user identification associated with each golfer that is usable by the golfer to access a remote server computer for uploading or downloading user data, and for modifying and adding shot, course and golf play information.

A user may download any rounds that are currently captured on, or inputted into, the device during golf play from remote device to the mobile device, either directly to the device itself or through a docketing or charging station. The software is operable to allow the user to verify the course and date, and then checks to confirm. When the user click-selects the "Confirm" button, the rounds are then available in the "Review Golf Round" screen, which is viewable on a display on a computer. On this screen view or graphic user interface, the software is operable to allow the user to select or indicate the round he wishes to review. The status of a round that has not been reviewed yet is preferably marked or noted as having the status of "Uploaded." A partially reviewed round will be indicated as "Changed," and a completely reviewed round is indicated as "Completed" on the user interface. In one embodiment of the present invention, the rounds will not be included in reports unless the round is completed.

In one embodiment all inputs, analytics, settings and other information is stored locally on the memory of the mobile device. In another embodiment, some or all inputs, analytics, settings and other information is stored on another computing device of the computer system, such as a remote computer, server or database. The mobile device may be connected to and the information stored therein accessible through a network during golf play, or, alternatively, may be connected to and the information stored therein accessible through a network when connected to the internet before and/or after golf play.

Certain modifications and improvements will occur to those skilled in the art upon a reading of the foregoing description. By way of example, automatic conversion between English units of measure (such as feet, yards) to metric equivalents may be included for user convenience. The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention and the following claims.

The invention claimed is:

1. A method for defining at least one target area for statistical analysis of golf performance comprising:
   providing a mobile device including a Global Positioning System (GPS) component;
   the GPS component determining GPS coordinates of a starting position, wherein the starting position is a location of the mobile device;
   the mobile device storing the GPS coordinates of the first starting position;
   the mobile device defining a recommended target area based on at least historical performance data for a club selection;
   the mobile device adjusting a position of the recommended target area to a location within range of the club selection;
   the mobile device converting the recommended target area to a custom target area based on manual input of positions, dimensions, and/or shapes for the custom target area; and
   the mobile device automatically modifying a perimeter of the custom target area such that the custom target area does not extend outside of fairway boundaries or green boundaries.

2. The method of claim 1, further comprising customizing the recommended target area in three dimensions based on the manual input.

3. The method of claim 1, wherein the mobile device defining the recommended target area is further based on a direction and range of distances from the starting position and/or weather conditions.

4. The method of claim 1, further providing a graphical user interface (GUI) and displaying via the GUI the starting position, the recommended target area, the custom target area, course features, the fairway boundaries, and green boundaries.

5. The method of claim 4, wherein the mobile device converting the recommended target area to a custom target area occurs through the GUI and includes confining the custom target area to a course feature.

6. The method of claim 4, further comprising the GUI displaying a second target area for a second shot, wherein the second target area is defined based on a direction and a range of distances from a resting ball location.

7. The method of claim 1, wherein the recommended target area includes multiple zones, wherein the multiple zones are based on the historical performance data for the club selection, wherein the historical performance data for the club selection includes shot zone diagrams for the club selection.

8. The method of claim 1, further comprising the mobile device receiving a resting ball location and the mobile device calculating whether the resting ball location is within the custom target area, and, if not, a distance, an elevation, and horizontal and vertical distances from the resting ball location to the custom target area.

9. The method of claim 8, further comprising the mobile device performing analytics, the analytics including providing text, tabular, graphic, and image based outputs that include trends information based upon the resting ball location and the custom target area, including the historical performance data for the club selection.

10. A method for defining at least one target for statistical analysis of golf performance comprising:
    providing a mobile device including a graphic user interface (GUI);
    the mobile device receiving a starting point;
    the mobile device creating a recommended target area based on the starting point;
    the mobile device multi-dimensionally adjusting position, dimensions, and/or shape of the recommended target area;
    the mobile device receiving customizable secondary target information and modifying a perimeter and a location of the recommended target area based on the customizable secondary target information to create a custom target area; and
    the mobile device automatically modifying the perimeter of the custom target area such that the custom target area does not extend outside of fairway boundaries or green boundaries.

11. The method of claim 10, further comprising confining the custom target area to a course feature.

12. The method of claim 10, further comprising the mobile device receiving a shot type and a club type and automatically positioning the recommended target area such that an average point of historical performance data for the club type is positioned centrally in the recommended target area.

13. The method of claim 10, wherein shot distances for the recommended target area are displayed via the GUI in multi-dimensional target zones having closed curve shapes.

14. The method of claim 13, wherein the multi-dimensional target zones are defined based on linear distances to the recommended target area as well as horizontal distances, vertical distances, or percent deviation from a target point within the target area.

15. The method of claim 10, wherein the recommended target area is created based on a club selection and/or weather conditions.

16. The method of claim 10, further comprising:
    the mobile device receiving a resting ball location;
    the mobile device determining whether the resting ball location is within the custom target area; and
    if the resting ball location is not within the custom target area, the mobile device determining a distance of the resting ball location from the custom target area and the mobile device calculating a percent error index.

17. A system for defining at least one target for statistical analysis of golf performance comprising:
    a device including a processor and a memory for storing software thereon;
    the device further including a Global Positioning System (GPS) component;
    the device operable to receive inputs including a starting position via the GPS component and/or via manual input;
    the device operable to store and retrieve player data, including historical performance data for a course or a club, both locally and on one or more cloud host servers;
    the device operable to generate a recommended target area, wherein the recommended target area is defined based on a direction and a range of distances from the first starting position and based on player data stored locally or in the one or more cloud host servers; and
    the device receiving a custom shape for the recommended target area and converting the recommended target area to a custom target area based on the custom shape;

the device modifying a perimeter of the custom target area such that the custom target area does not extend outside of fairway boundaries or green boundaries.

18. The system of claim 17, wherein the device is further operable to confine the recommended target area to additional course features.

19. The system of claim 17, wherein the recommended target area is created based on a club selection and/or weather conditions.

20. The system of claim 17, wherein the device is further operable to receive an input via a touchscreen including a selection of a point on a golf course and subsequently create and display the custom target area on a Graphical User Interface (GUI) based on the selection of the point on the golf course.

* * * * *